US007186408B2

(12) United States Patent
Alcami et al.

(10) Patent No.: US 7,186,408 B2
(45) Date of Patent: Mar. 6, 2007

(54) VIRAL CD30 POLYPEPTIDE

(75) Inventors: Antonio Alcami, Madrid (ES); Margarida Saraiva, London (GB)

(73) Assignee: Cambridge University Technical Services Limited, Cambridge (GB)

( * ) Notice: Subject to any disclaimer, the term of this patent is extended or adjusted under 35 U.S.C. 154(b) by 0 days.

(21) Appl. No.: 10/503,687

(22) PCT Filed: Feb. 6, 2003

(86) PCT No.: PCT/GB03/00530

§ 371 (c)(1), (2), (4) Date: Mar. 14, 2005

(87) PCT Pub. No.: WO03/066674

PCT Pub. Date: Aug. 14, 2003

(65) Prior Publication Data

US 2005/0222021 A1 Oct. 6, 2005

(30) Foreign Application Priority Data

Feb. 6, 2002 (GB) ................................ 0202769.6

(51) Int. Cl.
*A01N 63/00* (2006.01)
*A61K 39/275* (2006.01)
*A61K 83/00* (2006.01)

(52) U.S. Cl. ............... 424/93.1; 424/185.1; 424/186.1; 424/232.1

(58) Field of Classification Search ................ 530/350; 424/85.1; 435/69.1
See application file for complete search history.

(56) References Cited

OTHER PUBLICATIONS

Shchelkunov et al. Virol. 1998, vol. 243, No. 2, pp. 432-460.*

Stanciu et al. Respiratory Research 2005, vol. 6, No. 67, pp. 1-7.*

Legg et al. Am J. Respi. Crit. Care. Med. 2003, vol. 168, pp. 633-639.*

Lazar et al. Molecular and Cellular Biology 1988, vol. 8, No. 3, pp. 1247-1252.*

Smilek et al. Proc. Natl. Acad. Sci. USA, 1991, vol. 88, pp. 9633-9637.*

Horrie et al. Immunology 1998, vol. 10, pp. 457-470.*

Hamann et al. J. Immunol. 1996, vol. 156, pp. 1388-1391.*

Chen et al., "Analysis of host response modifier ORFs of ectromelia virus, the causative agent of mousepox," *Virus Research*, 66:155-173 (2000).

Panus et al., "Coxpox virus encodes a fifth member of the tumor necrosis factor receptor family: A soluable, secreted CD30 homologue," *PNAS*, 99(12):8348-8353 (2002).

Saraiva et al., "CrmE, a Novel Soluable Tumor Necrosis Factor Receptor Encoded by Poxviruses," *Journal of Virology*, 75(1):226-233 (2001).

Shchelkunov et al., "The Genomic Sequence Analysis of the Left and Right Species-Specific Terminal Region of a Cowpox Virus Strain Reveals Unique Sequences and a Cluster of Intact ORFs for Immunomodulatory and Host Range Proteins," *Virology*, 243:432-260 (1998).

Database EMBL 'Online', D13 L protein, *EBI Database accession* No. P87599, XP002248019, May 1, 1997.

* cited by examiner

*Primary Examiner*—Bruce R. Campell
*Assistant Examiner*—Bao Qun Li
(74) *Attorney, Agent, or Firm*—Klarquist Sparkman, LLP

(57) ABSTRACT

The present invention relates to the identification and characterisation of a viral homologue (vCD30) of mammalian CD30. The vCD30 polypeptide is shown to have immunomodulatory activity and has various therapeutic applications.

10 Claims, 10 Drawing Sheets

Figure 1 a

```
                SP
                ________________________
EV Hampstead    MKMNTIFLSAIVTCLVYTSFGKTCPNDYYLEPEDGLCKAC  40
EV Naval        MKMNTIFLSAIVTCLVYTSFGKTCPNDYYLEPEDGLCKAC  40
CPV-GRI90       MKMNTIFLSAIVTCLVYTSFGKTCPNDYYLEPEDGLCTAC  40

EV Hampstead    VTCLSNMVEIQSCGPDKPRKCQCGPGLKCMLPAVNSCARC  80
EV Naval        VTCLSNMVEIQSCGPDKPRKCQCGPGLKCTLPAVNSCARC  80
CPV-GRI90       VTCLSNMVEIQPCGPDKPRKCQCGPGLKCTVPAVNSCARC  80

EV Hampstead    TPDTTTKKIEPTEQCCTTPDNTKLCYHKYSS*  111
EV Naval        TPDTTTKKIEPTEQCCTTPDNTKLCYHKYSS*  111
CPV-GRI90       TPDTTIKKIEPTDQCCTTPDNTKLCYHKYSS*  111
```

[Sequence alignment figure showing Human, Mouse, and Viral protein sequences with conserved residues highlighted. The alignment includes labeled regions: SP (signal peptide) and TM (transmembrane domain), with position numbers at the right margin ranging from 20 to 595.]

FIGURE 2(a)

ATGAAGATGA ATACTATCTT TTTATCCGCT ATCGTAACCT GCCTAGTATA
TACATCATTT GGTAAAACGT GTCCTAATGA TTACTATCTT GAACCTGAAG
ATGGTTTATG TACGGCGTGT GTTACTTGTT TAAGCAATAT GGTAGAGATA
CAACCATGTG GACCGGATAA ACCACGAAAA TGTCAATGTG GTCCAGGATT
AAAATGTACG GTACCTGCAG TCAATAGTTG TGCCAGATGT ACTCCTGATA
CCACAATAAA GAAAATAGAA CCAACCGACC AATGCTGTAC CACTCCGGAT
AATACAAAAC TTTGTTATCA TAAATACTCA TCATGA

FIGURE 2(b)

ATGAAGATGA ATACTATCTT TTTATCCGCT ATCGTAACCT GCCTAGTATA
TACATCATTT GGTAAAACGT GTCCTAATGA TTACTATCTT GAACCTGAAG
ATGGTTTATG TAAGGCGTGT GTTACTTGTT TAAGCAATAT GGTAGAGATA
CAATCATGTG GTCCGGATAA ACCACGAAAA TGTCAATGTG GTCCAGGATT
GAAATGTATG CTGCCTGCCG TCAATAGTTG TGCAAGATGT ACTCCTGATA
CCACAACAAA GAAAATAGAA CCAACCGAAC AGTGCTGTAC CACTCCGGAT
AATACAAAAC TTTGTTATCA TAAATACTCA TCATGA

FIGURE 2(c)

ATGAAGATGA ATACTATCTT TTTATCCGCT ATCGTAACCT GCCTAGTATA
TACATCATTT GGTAAAACGT GTCCTAATGA TTACTATCTT GAACCTGAAG
ATGGTTTATG TAAGGCGTGT GTTACTTGTT TAAGCAATAT GGTAGAGATA
CAATCATGTG GTCCGGATAA ACCACGAAAA TGTCAATGTG GTCCAGGATT
GAAATGTACA CTGCCTGCCG TCAATAGTTG TGCAAGATGT ACTCCTGATA
CCACAACAAA GAAAATAGAA CCAACCGAAC AGTGCTGTAC CACTCCGGAT
AATACAAAAC TTTGTTATCA TAAATACTCA TCATGA

FIGURE 2(d)

ATGCGCGTCC TCCTCGCCGC GCTGGGACTG CTGTTCCTGG GGGCGCTACG
AGCCTTCCCA CAGGATCGAC CCTTCGAGGA CACCTGTCAT GGAAACCCCA
GCCACTACTA TGACAAGGCT GTCAGGAGGT GCTGTTACCG CTGCCCCATG
GGGCTGTTCC CGACACAGCA GTGCCCACAG AGGCCTACTG ACTGCAGGAA
GCAGTGTGAG CCTGACTACT ACCTGGATGA GGCCGACCGC TGTACAGCCT
GCGTGACTTG TTCTCGAGAT GACCTCGTGG AGAAGACGCC GTGTGCATGG
AACTCCTCCC GTGTCTGCGA ATGTCGACCC GGCATGTTCT GTTCCACGTC
TGCCGTCAAC TCCTGTGCCC GCTGCTTCTT CCATTCTGTC TGTCCGGCAG
GGATGATTGT CAAGTTCCCA GGCACGGCGC AGAAGAACAC GGTCTGTGAG
CCGGCTTCCC CAGGGGTCAG CCCTGCCTGT GCCAGCCCAG AGAACTGCAA
GGAACCCTCC AGTGGCACCA TCCCCCAGGC CAAGCCCACC CCGGTGTCCC
CAGCAACCTC CAGTGCCAGC ACCATGCCTG TAAGAGGGGG CACCCGCCTC
GCCCAGGAAG CTGCTTCTAA ACTGACGAGG GCTCCCGACT CTCCCTCCTC
TGTGGGAAGG CCTAGTTCAG ATCCAGGTCT GTCCCCAACA CAGCCATGCC
CAGAGGGGTC TGGTGATTGC AGAAAGCAGT GTGAGCCCGA CTACTACCTG
GACGAGGCCG GCCGCTGCAC AGCCTGCGTG AGCTGTTCTC GAGATGACCT
TGTGGAGAAG ACGCCATGTG CATGGAACTC CTCCCGCACC TGCGAATGTC
GACCTGGCAT GATCTGTGCC ACATCAGCCA CCAACTCCTG TGCCCGCTGT
GTCCCCTACC CAATCTGTGC AGCAGAGACG GTCACCAAGC CCCAGGATAT
GGCTGAGAAG GACACCACCT TTGAGGCGCC ACCCCTGGGG ACCCAGCCGG
ACTGCAACCC CACCCCAGAG AATGGCGAGG CGCCTGCCAG CACCAGCCCC
ACTCAGAGCT TGCTGGTGGA CTCCCAGGCC AGTAAGACGC TGCCCATCCC
AACCAGCGCT CCCGTCGCTC TCTCCTCCAC GGGGAAGCCC GTTCTGGATG
CAGGGCCAGT GCTCTTCTGG GTGATCCTGG TGTTGGTTGT GGTGGTCGGC
TCCAGCGCCT TCCTCCTGTG CCACCGGAGG GCCTGCAGGA AGCGAATTCG
GCAGAAGCTC CACCTGTGCT ACCCGGTCCA GACCTCCCAG CCCAAGCTAG
AGCTTGTGGA TTCCAGACCC AGGAGGAGCT CAACGCAGCT GAGGAGTGGT
GCGTCGGTGA CAGAACCCGT CGCGGAAGAG CGAGGGTTAA TGAGCCAGCC
ACTGATGGAG ACCTGCCACA GCGTGGGGGC AGCCTACCTG GAGAGCCTGC
CGCTGCAGGA TGCCAGCCCG GCCGGGGGCC CCTCGTCCCC CAGGGACCTT
CCTGAGCCCC GGGTGTCCAC GGAGCACACC AATAACAAGA TTGAGAAAAT
CTACATCATG AAGGCTGACA CCGTGATCGT GGGGACCGTG AAGGCTGAGC
TGCCGGAGGG CCGGGGCCTG GCGGGGCCAG CAGAGCCCGA GTTGGAGGAG
GAGCTGGAGG CGGACCATAC CCCCCACTAC CCCGAGCAGG AGACAGAACC
GCCTCTGGGC AGCTGCAGCG ATGTCATGCT CTCAGTGGAA GAGGAAGGGA
AAGAAGACCC CTTGCCCACA GCTGCCTCTG GAAAGTGA

FIGURE 2(e)

ATGAGCGCCC TACTCACCGC AGCGGGGTTG CTGTTCCTGG GGATGCTTCA
AGCCTTCCCA ACGGATCGAC CACTCAAGAC CACCTGTGCC GGAGACCTCA
GCCACTACCC AGGGGAGGCT GCCAGGAACT GCTGTTACCA GTGCCCCTCA
GGGTTGTCTC CGACACAGCC ATGCCCACGG GGTCCTGCCC ACTGCAGGAA
GCAGTGTGCA CCTGACTACT ACGTCAATGA AGACGGGAAG TGCACAGCCT
GCGTGACCTG TTTGCCAGGC CTTGTGGAGA AGGCTCCGTG TTCCGGGAAC
TCTCCTCGAA TCTGTGAGTG TCAGCCTGGC ATGCACTGCT GCACACCAGC
AGTCAATTCC TGCGCCCGCT GCAAACTCCA CTGTTCTGGA GAGGAGGTTG
TCAAGTCTCC AGGCACAGCA AAGAAGGACA CTATCTGTGA GCTGCCTTCC
TCGGGATCTG GTCCCAATTG CTCCAATCCG GGTGACCGCA AGACACTTAC
TAGCCATGCC ACTCCTCAGG CCATGCCTAC TCTAGAATCC CCAGCCAATG
ACAGTGCAAG GAGCTTGCTG CCAATGCGTG TCACCAACCT TGTGCAGGAA
GATGCTACTG AGTTGGTGAA GGTTCCAGAA TCTTCCTCGT CCAAGGCAAG
GGAGCCCAGT CCAGATCCAG GTAATGCAGA GAAGAATATG ACCTTGGAGC
TTCCATCTCC AGGGACACTC CCTGACATCA GCACCTCAGA AAACAGCAAG
GAGCCTGCAA GTACCGCCTC CACCCTAAGC CTTGTGGTAG ATGCCTGGAC
CAGCAGCAGG ATGCAGCCCA CCTCTCCATT GTCCACGGGA ACACCATTTC
TGGATCCAGG GCCCGTGCTC TTCTGGGTGG CCATGGTGGT GCTACTGGTT
GGCTCCGGCT CCTTTCTCCT GTGTTACTGG AAGGCCTGTA GGAGGCGGTT
CCAGCAGAAG TTTCACCTGG ACTACCTAGT GCAGACCTTC CAGCCCAAGA
TGGAGCAGAC AGATTCCTGT CCTACTGAAA AGCTAACCCA GCCACAGAGA
AGCGGGTCGG TGACAGATCC CAGCACGGGA CACAAGTTGA GCCCAGTGAG
CCCTCCTCCA GCTGTAGAGA CTTGTGCCAG TGTTGGGGCC ACCTACCTGG
AGAACCTGCC GCTGCTGGAT GACAGCCCAG CTGGGAATCC CTTTTCTCCC
AGGGAACCTC CAGAGCCCCG GGTATCCACG GAACACACCA ATAACAGGAT
TGAGAAAATC TACATCATGA AGGCCGACAC AGTGATCGTG GGCTCTGTAA
AAACTGAAGT CCCTGAGGGC CGGGCTCCAG CAGGGTCTAC AGAGTCTGAG
TTGGAAGCTG AACTAGAAGT GGACCATGCC CCCCATTACC CGGAGCAGGA
GACAGAACCA CCTCTGGGCA GCTGCACTGA GGTCATGTTC TCGGTGGAGG
AAGGAGGAAA AGAGGACCAT GGGCCCACGA CTGTCTCTGA GAAGTGA

Figure 5
a
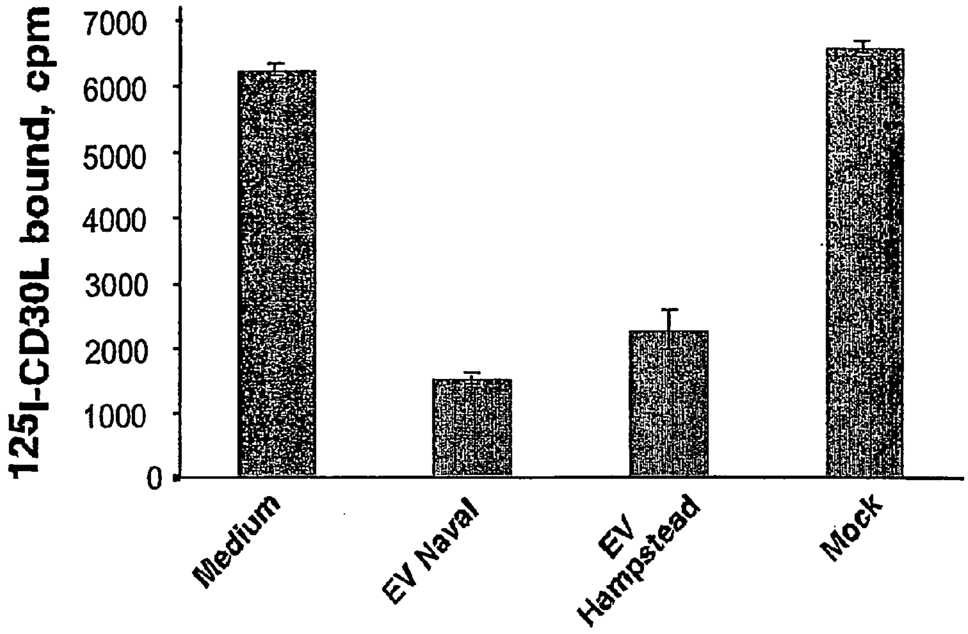
b
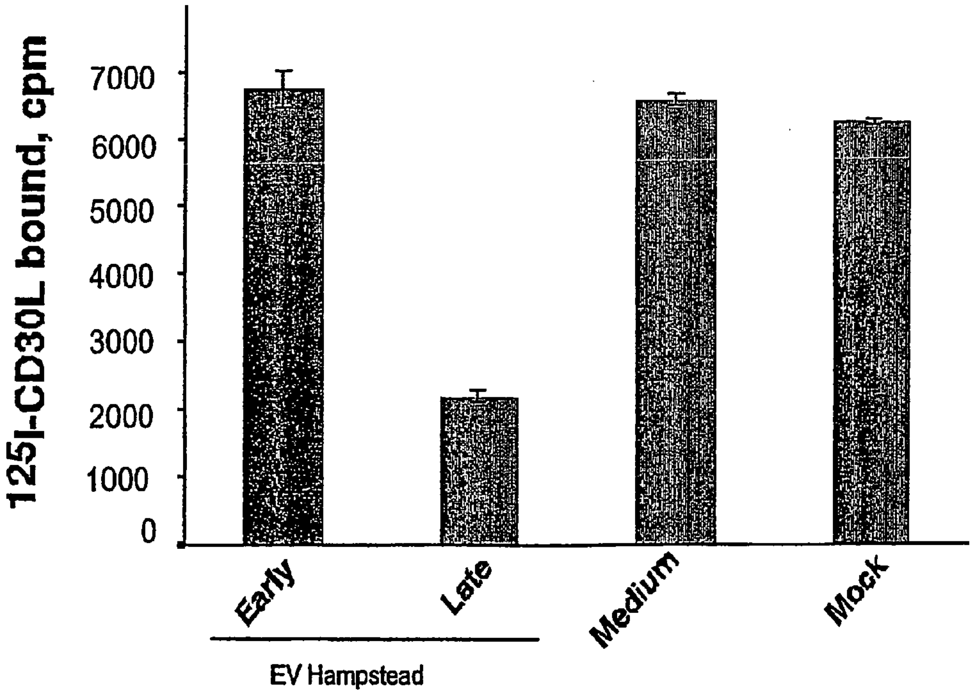

SEQUENCE LISTING

<160> NUMBER OF SEQ ID NOS: 15

<210> SEQ ID NO 1
<211> LENGTH: 111
<212> TYPE: PRT
<213> ORGANISM: Ectromelia virus

<400> SEQUENCE: 1

Met Lys Met Asn Thr Ile Phe Leu Ser Ala Ile Val Thr Cys Leu Val
1 5 10 15

Tyr Thr Ser Phe Gly Lys Thr Cys Pro Asn Asp Tyr Tyr Leu Glu Pro
20 25 30

Glu Asp Gly Leu Cys Lys Ala Cys Val Thr Cys Leu Ser Asn Met Val
35 40 45

Glu Ile Gln Ser Cys Gly Pro Asp Lys Pro Arg Lys Cys Gln Cys Gly
50 55 60

Pro Gly Leu Lys Cys Met Leu Pro Ala Val Asn Ser Cys Ala Arg Cys
65 70 75 80

Thr Pro Asp Thr Thr Thr Lys Lys Ile Glu Pro Thr Glu Gln Cys Cys
85 90 95

Thr Thr Pro Asp Asn Thr Lys Leu Cys Tyr His Lys Tyr Ser Ser
100 105 110

<210> SEQ ID NO 2
<211> LENGTH: 111
<212> TYPE: PRT
<213> ORGANISM: Ectromelia virus

<400> SEQUENCE: 2

Met Lys Met Asn Thr Ile Phe Leu Ser Ala Ile Val Thr Cys Leu Val
1 5 10 15

Tyr Thr Ser Phe Gly Lys Thr Cys Pro Asn Asp Tyr Tyr Leu Glu Pro
20 25 30

Glu Asp Gly Leu Cys Lys Ala Cys Val Thr Cys Leu Ser Asn Met Val
35 40 45

Glu Ile Gln Ser Cys Gly Pro Asp Lys Pro Arg Lys Cys Gln Cys Gly
50 55 60

Pro Gly Leu Lys Cys Thr Leu Pro Ala Val Asn Ser Cys Ala Arg Cys
65 70 75 80

Thr Pro Asp Thr Thr Thr Lys Lys Ile Glu Pro Thr Glu Gln Cys Cys
85 90 95

Thr Thr Pro Asp Asn Thr Lys Leu Cys Tyr His Lys Tyr Ser Ser
100 105 110

<210> SEQ ID NO 3
<211> LENGTH: 111
<212> TYPE: PRT
<213> ORGANISM: Cowpox virus

<400> SEQUENCE: 3

Met Lys Met Asn Thr Ile Phe Leu Ser Ala Ile Val Thr Cys Leu Val
1 5 10 15

Tyr Thr Ser Phe Gly Lys Thr Cys Pro Asn Asp Tyr Tyr Leu Glu Pro
20 25 30

Glu Asp Gly Leu Cys Thr Ala Cys Val Thr Cys Leu Ser Asn Met Val
35 40 45

-continued

```
Glu Ile Gln Pro Cys Gly Pro Asp Lys Pro Arg Lys Cys Gln Cys Gly
    50                  55                  60

Pro Gly Leu Lys Cys Thr Val Pro Ala Val Asn Ser Cys Ala Arg Cys
65                  70                  75                  80

Thr Pro Asp Thr Thr Ile Lys Lys Ile Glu Pro Thr Asp Gln Cys Cys
                85                  90                  95

Thr Thr Pro Asp Asn Thr Lys Leu Cys Tyr His Lys Tyr Ser Ser
            100                 105                 110


<210> SEQ ID NO 4
<211> LENGTH: 595
<212> TYPE: PRT
<213> ORGANISM: Homo sapiens

<400> SEQUENCE: 4

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320
```

-continued

```
Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595


<210> SEQ ID NO 5
<211> LENGTH: 498
<212> TYPE: PRT
<213> ORGANISM: Mus sp.

<400> SEQUENCE: 5

Met Ser Ala Leu Leu Thr Ala Ala Gly Leu Leu Phe Leu Gly Met Leu
1               5                   10                  15

Gln Ala Phe Pro Thr Asp Arg Pro Leu Lys Thr Thr Cys Ala Gly Asp
            20                  25                  30

Leu Ser His Tyr Pro Gly Glu Ala Ala Arg Asn Cys Cys Tyr Gln Cys
        35                  40                  45

Pro Ser Gly Leu Ser Pro Thr Gln Pro Cys Pro Arg Gly Pro Ala His
    50                  55                  60

Cys Arg Lys Gln Cys Ala Pro Asp Tyr Tyr Val Asn Glu Asp Gly Lys
65                  70                  75                  80

Cys Thr Ala Cys Val Thr Cys Leu Pro Gly Leu Val Glu Lys Ala Pro
                85                  90                  95
```

-continued

```
Cys Ser Gly Asn Ser Pro Arg Ile Cys Glu Cys Gln Pro Gly Met His
            100                 105                 110

Cys Cys Thr Pro Ala Val Asn Ser Cys Ala Arg Cys Lys Leu His Cys
        115                 120                 125

Ser Gly Glu Glu Val Val Lys Ser Pro Gly Thr Ala Lys Lys Asp Thr
    130                 135                 140

Ile Cys Glu Leu Pro Ser Ser Gly Ser Gly Pro Asn Cys Ser Asn Pro
145                 150                 155                 160

Gly Asp Arg Lys Thr Leu Thr Ser His Ala Thr Pro Gln Ala Met Pro
                165                 170                 175

Thr Leu Glu Ser Pro Ala Asn Asp Ser Ala Arg Ser Leu Leu Pro Met
            180                 185                 190

Arg Val Thr Asn Leu Val Gln Glu Asp Ala Thr Glu Leu Val Lys Val
        195                 200                 205

Pro Glu Ser Ser Ser Ser Lys Ala Arg Glu Pro Ser Pro Asp Pro Gly
    210                 215                 220

Asn Ala Glu Lys Asn Met Thr Leu Glu Leu Pro Ser Pro Gly Thr Leu
225                 230                 235                 240

Pro Asp Ile Ser Thr Ser Glu Asn Ser Lys Glu Pro Ala Ser Thr Ala
                245                 250                 255

Ser Thr Leu Ser Leu Val Val Asp Ala Trp Thr Ser Ser Arg Met Gln
            260                 265                 270

Pro Thr Ser Pro Leu Ser Thr Gly Thr Pro Phe Leu Asp Pro Gly Pro
        275                 280                 285

Val Leu Phe Trp Val Ala Met Val Val Leu Leu Val Gly Ser Gly Ser
    290                 295                 300

Phe Leu Leu Cys Tyr Trp Lys Ala Cys Arg Arg Arg Phe Gln Gln Lys
305                 310                 315                 320

Phe His Leu Asp Tyr Leu Val Gln Thr Phe Gln Pro Lys Met Glu Gln
                325                 330                 335

Thr Asp Ser Cys Pro Thr Glu Lys Leu Thr Gln Pro Gln Arg Ser Gly
            340                 345                 350

Ser Val Thr Asp Pro Ser Thr Gly His Lys Leu Ser Pro Val Ser Pro
        355                 360                 365

Pro Pro Ala Val Glu Thr Cys Ala Ser Val Gly Ala Thr Tyr Leu Glu
    370                 375                 380

Asn Leu Pro Leu Leu Asp Asp Ser Pro Ala Gly Asn Pro Phe Ser Pro
385                 390                 395                 400

Arg Glu Pro Pro Glu Pro Arg Val Ser Thr Glu His Thr Asn Asn Arg
                405                 410                 415

Ile Glu Lys Ile Tyr Ile Met Lys Ala Asp Thr Val Ile Val Gly Ser
            420                 425                 430

Val Lys Thr Glu Val Pro Glu Gly Arg Ala Pro Ala Gly Ser Thr Glu
        435                 440                 445

Ser Glu Leu Glu Ala Glu Leu Glu Val Asp His Ala Pro His Tyr Pro
    450                 455                 460

Glu Gln Glu Thr Glu Pro Pro Leu Gly Ser Cys Thr Glu Val Met Phe
465                 470                 475                 480

Ser Val Glu Glu Gly Gly Lys Glu Asp His Gly Pro Thr Thr Val Ser
                485                 490                 495

Glu Lys
```

-continued

<210> SEQ ID NO 6
<211> LENGTH: 336
<212> TYPE: DNA
<213> ORGANISM: Cowpox virus

<400> SEQUENCE: 6
atgaagatga atactatctt tttatccgct atcgtaacct gcctagtata tacatcattt 60
ggtaaaacgt gtcctaatga ttactatctt gaacctgaag atggtttatg tacggcgtgt 120
gttacttgtt taagcaatat ggtagagata caaccatgtg gaccggataa accacgaaaa 180
tgtcaatgtg gtccaggatt aaaatgtacg gtacctgcag tcaatagttg tgccagatgt 240
actcctgata ccacaataaa gaaaatagaa ccaaccgacc aatgctgtac cactccggat 300
aatacaaaac tttgttatca taaatactca tcatga 336

<210> SEQ ID NO 7
<211> LENGTH: 336
<212> TYPE: DNA
<213> ORGANISM: Ectromelia virus

<400> SEQUENCE: 7
atgaagatga atactatctt tttatccgct atcgtaacct gcctagtata tacatcattt 60
ggtaaaacgt gtcctaatga ttactatctt gaacctgaag atggtttatg taaggcgtgt 120
gttacttgtt taagcaatat ggtagagata caatcatgtg gtccggataa accacgaaaa 180
tgtcaatgtg gtccaggatt gaaatgtatg ctgcctgccg tcaatagttg tgcaagatgt 240
actcctgata ccacaacaaa gaaaatagaa ccaaccgaac agtgctgtac cactccggat 300
aatacaaaac tttgttatca taaatactca tcatga 336

<210> SEQ ID NO 8
<211> LENGTH: 336
<212> TYPE: DNA
<213> ORGANISM: Ectromelia virus

<400> SEQUENCE: 8
atgaagatga atactatctt tttatccgct atcgtaacct gcctagtata tacatcattt 60
ggtaaaacgt gtcctaatga ttactatctt gaacctgaag atggtttatg taaggcgtgt 120
gttacttgtt taagcaatat ggtagagata caatcatgtg gtccggataa accacgaaaa 180
tgtcaatgtg gtccaggatt gaaatgtaca ctgcctgccg tcaatagttg tgcaagatgt 240
actcctgata ccacaacaaa gaaaatagaa ccaaccgaac agtgctgtac cactccggat 300
aatacaaaac tttgttatca taaatactca tcatga 336

<210> SEQ ID NO 9
<211> LENGTH: 1788
<212> TYPE: DNA
<213> ORGANISM: Homo sapiens

<400> SEQUENCE: 9
atgcgcgtcc tcctcgccgc gctgggactg ctgttcctgg gggcgctacg agccttccca 60
caggatcgac ccttcgagga cacctgtcat ggaaacccca gccactacta tgacaaggct 120
gtcaggaggt gctgttaccg ctgccccatg ggctgttcc cgacacagca gtgcccacag 180
aggcctactg actgcaggaa gcagtgtgag cctgactact acctggatga ggccgaccgc 240
tgtacagcct gcgtgacttg ttctcgagat gacctcgtgg agaagacgcc gtgtgcatgg 300
aactcctccc gtgtctgcga atgtcgaccc ggcatgttct gttccacgtc tgccgtcaac 360

-continued

```
tcctgtgccc gctgcttctt ccattctgtc tgtccggcag ggatgattgt caagttccca    420

ggcacggcgc agaagaacac ggtctgtgag ccggcttccc caggggtcag ccctgcctgt    480

gccagcccag agaactgcaa ggaaccctcc agtggcacca tcccccaggc caagcccacc    540

ccggtgtccc cagcaacctc cagtgccagc accatgcctg taagaggggg cacccgcctc    600

gcccaggaag ctgcttctaa actgacgagg gctcccgact ctccctcctc tgtgggaagg    660

cctagttcag atccaggtct gtccccaaca cagccatgcc cagaggggtc tggtgattgc    720

agaaagcagt gtgagcccga ctactacctg gacgaggccg gccgctgcac agcctgcgtg    780

agctgttctc gagatgacct tgtggagaag acgccatgtg catggaactc ctcccgcacc    840

tgcgaatgtc gacctggcat gatctgtgcc acatcagcca ccaactcctg tgcccgctgt    900

gtcccctacc caatctgtgc agcagagacg gtcaccaagc cccaggatat ggctgagaag    960

gacaccacct ttgaggcgcc acccctgggg acccagccgg actgcaaccc caccccagag   1020

aatggcgagg cgcctgccag caccagcccc actcagagct tgctggtgga ctcccaggcc   1080

agtaagacgc tgcccatccc aaccagcgct cccgtcgctc tctcctccac ggggaagccc   1140

gttctggatg cagggccagt gctcttctgg gtgatcctgg tgttggttgt ggtggtcggc   1200

tccagcgcct tcctcctgtg ccaccggagg gcctgcagga agcgaattcg gcagaagctc   1260

cacctgtgct acccggtcca gacctcccag cccaagctag agcttgtgga ttccagaccc   1320

aggaggagct caacgcagct gaggagtggt gcgtcggtga cagaacccgt cgcggaagag   1380

cgagggttaa tgagccagcc actgatggag acctgccaca gcgtgggggc agcctacctg   1440

gagagcctgc cgctgcagga tgccagcccg gccgggggcc cctcgtcccc cagggacctt   1500

cctgagcccc gggtgtccac ggagcacacc aataacaaga ttgagaaaat ctacatcatg   1560

aaggctgaca ccgtgatcgt ggggaccgtg aaggctgagc tgccggaggg ccggggcctg   1620

gcggggccag cagagcccga gttggaggag gagctggagg cggaccatac cccccactac   1680

cccgagcagg agacagaacc gcctctgggc agctgcagcg atgtcatgct ctcagtggaa   1740

gaggaaggga aagaagaccc cttgcccaca gctgcctctg gaaagtga                1788
```

<210> SEQ ID NO 10
<211> LENGTH: 1497
<212> TYPE: DNA
<213> ORGANISM: Mus sp.

<400> SEQUENCE: 10

```
atgagcgccc tactcaccgc agcggggttg ctgttcctgg ggatgcttca agccttccca     60

acggatcgac cactcaagac cacctgtgcc ggagacctca gccactaccc aggggaggct    120

gccaggaact gctgttacca gtgcccctca gggttgtctc cgacacagcc atgcccacgg    180

ggtcctgccc actgcaggaa gcagtgtgca cctgactact acgtcaatga agacgggaag    240

tgcacagcct gcgtgacctg tttgccaggc cttgtggaga aggctccgtg ttccgggaac    300

tctcctcgaa tctgtgagtg tcagcctggc atgcactgct gcacaccagc agtcaattcc    360

tgcgcccgct gcaaactcca ctgttctgga gaggaggttg tcaagtctcc aggcacagca    420

aagaaggaca ctatctgtga gctgccttcc tcgggatctg gtcccaattg ctccaatccg    480

ggtgaccgca agacacttac tagccatgcc actcctcagg ccatgcctac tctagaatcc    540

ccagccaatg acagtgcaag gagcttgctg ccaatgcgtg tcaccaacct tgtgcaggaa    600

gatgctactg agttggtgaa ggttccagaa tcttcctcgt ccaaggcaag ggagcccagt    660

ccagatccag gtaatgcaga gaagaatatg accttggagc ttccatctcc agggacactc    720
```

-continued

```
cctgacatca gcacctcaga aaacagcaag gagcctgcaa gtaccgcctc caccctaagc    780

cttgtggtag atgcctggac cagcagcagg atgcagccca cctctccatt gtccacggga    840

acaccatttc tggatccagg gcccgtgctc ttctgggtgg ccatggtggt gctactggtt    900

ggctccggct cctttctcct gtgttactgg aaggcctgta ggaggcggtt ccagcagaag    960

tttcacctgg actacctagt gcagaccttc cagcccaaga tggagcagac agattcctgt   1020

cctactgaaa agctaaccca gccacagaga agcgggtcgg tgacagatcc cagcacggga   1080

cacaagttga gcccagtgag ccctcctcca gctgtagaga cttgtgccag tgttggggcc   1140

acctacctgg agaacctgcc gctgctggat gacagcccag ctgggaatcc cttttctccc   1200

agggaacctc cagagccccg ggtatccacg gaacacacca ataacaggat tgagaaaatc   1260

tacatcatga aggccgacac agtgatcgtg ggctctgtaa aaactgaagt ccctgagggc   1320

cgggctccag cagggtctac agagtctgag ttggaagctg aactagaagt ggaccatgcc   1380

ccccattacc cggagcagga gacagaacca cctctgggca gctgcactga ggtcatgttc   1440

tcggtggagg aaggaggaaa agaggaccat gggcccacga ctgtctctga gaagtga      1497
```

<210> SEQ ID NO 11
<211> LENGTH: 21
<212> TYPE: DNA
<213> ORGANISM: Artificial sequence
<220> FEATURE:
<223> OTHER INFORMATION: Oligonucleotide CD30-1

<400> SEQUENCE: 11

```
gttctggata catgcacaaa g                                                21
```

<210> SEQ ID NO 12
<211> LENGTH: 22
<212> TYPE: DNA
<213> ORGANISM: Artificial sequence
<220> FEATURE:
<223> OTHER INFORMATION: Oligonucleotide CD30-2

<400> SEQUENCE: 12

```
ggaggataat catttgcaaa cg                                               22
```

<210> SEQ ID NO 13
<211> LENGTH: 41
<212> TYPE: DNA
<213> ORGANISM: Artificial sequence
<220> FEATURE:
<223> OTHER INFORMATION: Oligonucleotide CD30-3

<400> SEQUENCE: 13

```
cgcaagcttg gatccatgaa gatgaatact atctttttat c                          41
```

<210> SEQ ID NO 14
<211> LENGTH: 35
<212> TYPE: DNA
<213> ORGANISM: Artificial sequence
<220> FEATURE:
<223> OTHER INFORMATION: Oligonucleotide CD30-4

<400> SEQUENCE: 14

```
cgcgcggccg ctgatgagta tttatgataa caaag                                 35
```

<210> SEQ ID NO 15
<211> LENGTH: 36
<212> TYPE: DNA
<213> ORGANISM: Artificial sequence -continued

```
<220> FEATURE:
<223> OTHER INFORMATION: Oligonucleotide CD30-5

<400> SEQUENCE: 15

cgcggtacct catgatgagt atttatgata acaaag                          36
```

VIRAL CD30 POLYPEPTIDE

CROSS REFERENCE TO RELATED APPLICATIONS

This is a § 371 U.S. national stage of PCT/GB03/00530, filed Feb. 6, 2003, which was published in English under PCT Article 2(2), and claims the benefit of Great Britain application 0202769.6, filed Feb. 6, 2002. Both applications are incorporated herein in their entirety.

The present invention relates to the identification and characteristion of a viral homologue (vCD30) of mammalian CD30. This work has various therapeutic applications which are provided herein.

CD30 and CD30L (CD153) are members of the tumour necrosis factor receptor (TNFR) and TNF superfamilies, respectively. CD30 was first identified by the monoclonal antibody (mAb) Ki-1 against Hodgkin and Reed-Sternberg cells (Schwab, U. et al. *Nature* 299, 65–67 (1982)), the malignant component of Hodgkin's disease, and has been extensively used as a clinical disease marker. CD30 was subsequently found in resting $CD8^+$ T cells, activated or virally transformed T and B cells and at the surface of HIV-infected lymphocytes.

CD30 is a type I membrane protein which can be cleaved by metalloproteases producing a soluble form (sCD30) (Horie, R. & Watanabe, T. *Semin. Immunol.* 10, 457–470 (1998)). The extracellular domain of CD30 shows cysteine rich domains (CRDs) characteristic of the TNFR superfamily. CD30L is expressed as a type II membrane glycoprotein (Horie, R. & Watanabe, T. *Semin. Immunol.* 10, 457–470 (1998)) in resting neutrophils and B cells, activated T cells and macrophages, and in neoplastic cells such as Burkitt-type lymphoma cells or B cells associated with lymphoproliferative disorders. The extracellular domain of CD30L shows homology to TNF, lymphotoxin and CD40L (Smith, C. A. et al. *Cell* 73, 1349–1360 (1993)). It is unclear whether CD30L also exists as a soluble form.

Interaction of CD30L with cells expressing CD30 induces signals mediated by NF-KB and TRAF2 that cause cell proliferation or cell death. Interestingly, upon binding CD30, CD30L is also able to signal. One of the consequences of this reverse signalling is cell proliferation (Wiley, S. R. et al *J. Immuno.l* 157, 3635–3639 (1996)).

The role of the CD30/CD30L interaction in health and disease is still not totally understood, in part due to the pleiotropic nature of CD30 signals. Mice lacking a functional CD30 gene show defective negative thymocyte selection (Amakawa, R. et al. *Cell* 84, 551–562 (1996)), whereas transgenic mice expressing CD30 in the thymus have enhanced thymic negative selection (Chiarle, R. et al. *J. Immunol.* 163, 194–205 (1999)).

A recent study of genes targeted by CD30 indicates that Fas, TRAIL, CCR7, TRAF1 and cIAP2 are up-regulated while FasL, perforin, granzyme B and c-myc are down-regulated (Muta, H. et al *J. Immunol.* 165, 5105–5111 (2000)). Increased levels of sCD30 are observed in malignant lymphomas, viral infection (HIV, human T-cell leukemia virus and Epstein-Barr virus) and several immunological disorders, such as systemic lupus erythematosus or rheumatoid arthritis, although the reason for this is not known (Gruss, H. J. et al *Immunol. Today* 18, 156–163 (1997)).

Poxviruses are a family of complex DNA viruses that encode up to 200 genes and infect a wide variety of hosts (Moss, B. *Poxyiridae: the virus and their replication, in Virology*. (ed. B. N. Fields et al) 2637–2671 (Raven Publishers, Philadelphia, Pa., 1996)). Examples include variola, vaccinia, cowpox and ectromelia virus. Smallpox was a devastating disease caused by variola virus (VaV), a poxvirus which is one of the most virulent human pathogens. Vaccinia virus (VV) is the best characterized poxvirus and was used as a vaccine to achieve the global eradication of smallpox by 1977. However, the origin and natural host of vaccinia virus are unknown. Cowpox virus (CPV) is probably a rodent virus that sporadically infects other animal species. Ectromelia virus (EV) is a highly virulent natural pathogen of mice that causes mousepox and has been isolated from outbreaks in laboratory mouse colonies (Fenner, F. & Buller, R. M. *Mousepox, in Viral Pathogenesis*. (ed. N. Nathanson) 535–553 (Lippincott-Raven Publishers, Philadelphia, Pa., 1997). Like VaV, EV has a restricted host range and causes severe disease with high mortality rate and skin lesions in the later stages of infection. Similarities with smallpox make EV an interesting experimental model for virus-host interactions.

Poxviruses encode a unique collection of genes that evade host immune responses. These molecules are often secreted and include cytokine homologues and soluble cytokine receptors or binding proteins (Alcami, A. & Koszinowski, U. H. *Immunol. Today* 21, 447–455 (2000), McFadden, G. & Murphy, P. M. *Curr. Opin. Microbiol.* 3, 371–378 (2000), Tortorella, D. et al *Annu. Rev. Immunol.* 18, 861–926 (2000)). Some of these viral genes seem to have been acquired from the host and modified during virus evolution to confer an advantage for virus replication, survival or transmission. EV encodes receptors or binding proteins for TNF (Loparev, V. N. et al. *Proc. Natl. Acad. Sci. U.S.A.* 95, 3786–3791 (1998)), interleukin (IL)-1β, (Smith, V. P. & Alcami, A. *J. Virol.* 74, 8460–8471 (2000)), interferon (IFN)-γ (Mossman, K. et al. *Virology* 208, 762–769 (1995), Smith, V. P. & Alcami, A. *J. Virol.* 76, in press (2001)), IFN-α/β (Colamonici, O. R. et al *J. Biol. Chem.* 270, 15974–15978 (1995)), IL-18 (Smith, V. P. et al *J. Gen. Virol.* 81, 1223–1230 (2000), Born, T. L. et al. *J. Immunol.* 164, 3246–3254 (2000)) and chemokines (Graham, K. A. et al. *Virology* 229, 12–24 (1997)). EV also encodes anti-apoptotic proteins (Turner, S. J. et al *J. Gen. Virol.* 81, 2425–2430 (2000), Brick, D. J. et al *J. Gen. Virol.* 81, 1087–1097 (2000)) and an intracellular protein that confers IFN resistance (Smith, V. P. & Alcami, A (2001) supra).

The TNF binding activity encoded by orthopoxviruses is particularly interesting since there are four distinct viral (v)TNFRs: CrmB (Hu, F. Q. et al *Virology* 204, 343–356 (1994)), CrmC (Smith, C. A. et al. *Virology* 223, 132–147 (1996)), CrmD (Loparev, V. N. et al (1998) supra) and CrmE (Saraiva, M. & Alcami, A. J. Virol. 75, 226–233 (2001)).

These molecules show different ligand specificity and are expressed at different times post-infection (p.i.), but their relative contribution to viral pathogenesis is not well understood.

The present inventors have found that certain poxviruses, in particular ectromelia (mousepox) virus and cowpox virus, express a novel member of the TNFR superfamily (vCD30: viral CD30), which is a homologue of mammalian CD30. vCD30 has been found to block CD30/CD30L binding and induce reverse signalling in CD30L expressing cells. In addition, using vCD30, the present inventors have identified a role of CD30 in modulating Th1 immune responses.

According to one aspect of the present invention there is provided an isolated vCD30 polypeptide which comprises or consists of an amino acid sequence shown in FIG. 1(*a*).

Another aspect of the present invention provides an isolated vCD30 polypeptide which is an amino acid sequence variant, allele, derivative or mutant of the sequence shown in FIG. 1(*a*). Such a polypeptide may have an amino acid sequence which differs from that given in FIG. 1(*a*) by one or more of addition, substitution, deletion and insertion of one or more amino acids.

A vCD30 polypeptide may be a viral polypeptide, more preferably a poxvirus polypeptide, for example a polypeptide from ectromelia (mousepox) virus or cowpox virus.

A polypeptide which is an amino acid sequence variant, allele, derivative or mutant of the amino acid sequence shown in FIG. 1(*a*) may comprise an amino acid sequence which differs from that shown in FIG. 1(*a*) but which shares greater than about 35% sequence identity with the sequence shown in FIG. 1, greater than about 40%, greater than about 50%, greater than about 60%, greater than about 70%, greater than about 80%, greater than about 90% or greater than about 95%. The sequence may share greater than about 40% similarity, greater than about 45% similarity, greater than about 50% similarity, greater than about 60% similarity, greater than about 65% similarity, greater than about 70% similarity, greater than about 80% similarity or greater than about 90% similarity with the amino acid sequence shown in the FIG. 1(*a*).

Amino acid similarity and homology are generally defined with reference to the algorithm GAP (Genetics Computer Group, Madison, Wis.). GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN(which use the method of Altschul et al. (1990) *J. Mol. Biol.* 215: 405–410), FASTA (which uses the method of Pearson and Lipman (1988) *PNAS USA* 85: 2444–2448), or the Smith-Waterman algorithm (Smith and Waterman (1981) *J. Mol. Biol.* 147: 195–197), generally employing default parameters.

Similarity allows for "conservative variation", i.e. substitution of one hydrophobic residue such as isoleucine, valine, leucine or methionine for another; or the substitution of one polar residue for another, such as arginine for lysine, glutamic for aspartic acid, or glutamine for asparagine.

Particular amino acid sequence variants may differ from that shown in FIG. 1(*a*) herein by insertion, addition, substitution or deletion of 1 amino acid, 2, 3, 4, 5–10, 10–20 20–30, 30–50 or 50–100 amino acids.

For example, a polypeptide may have an amino acid substitution at one or more of residues 38, 52, 70, 71, 86 and 93 of an sequence shown in FIG. 1(*a*) or residues corresponding thereto. For example, residue 38 may be Lys or Thr, residue 52 may be Pro or Ser, residue 70 may be Met or Thr, residue 71 may be Leu or Val residue 86 may be Ile or Thr and residue 93 may be Asp or Glu.

Preferred vCD30 polypeptides may comprise one or more of the following residues; Leu8, Ser9, Cys14, Thr18, Lys22, Cys24, Asp27, Tyr28, Tyr29, Leu30, Glu33, Asp34, Gly35, Cys37, Ala39, Cys40, Val41, Thr42, Cys43, Leu44, Val48, Glu49, Cys53, Pro58, ArgS9, Cys61, Cys63, Pro65, Gly66, Cys69, Pro72, Ala73, Val74, Asn75, Ser76, Cys77, Ala78, Arg79, Cys80, Glu90, Thr97, Asn101, Thr102, Cys105 and Ser110. Particularly preferred polypeptides may comprise any combination of two, three, four five, six, seven, eight, nine or ten or more of these residues.

Residues are numbered in relation to the initiating Met residue, which has the number 1. It will be appreciated that because of variations in sequence, the equivalent or corresponding residues in other vCD30 polypeptide sequences may have different numbers. Reference herein to a residue numbered according to a sequence of FIG. 1(*a*) is understood to include the equivalent residue in other vCD30 polypeptide sequences.

Another aspect of the present invention provides a fragment of a full-length vCD30 polypeptide sequence, for example a polypeptide fragment of any one of the three vCD30 amino acid sequences of 111 amino acids (EV Hampstead, EV Naval or CPV-Gri90) which are shown in FIG. 1(*a*).

A "fragment" of a polypeptide generally means a stretch of amino acid residues of less than 111 amino acids, for example less than 100 amino acids, less than 90 amino acids, less than 80 amino acids, less than 70 amino acids, less than 60 amino acids or less than 50 amino acids. A fragment will generally consist of at least 5 amino acids, for example at least 7 amino acids, at least 10 amino acids, at least 15 amino acids, at least 20 amino acids, at least 25 amino acids, at least 30 amino acids or at least 35 amino acids.

Preferred fragments are less than the full-length vCD30 polypeptide (i.e. consist of fewer amino acid residues; for example, less than 111 amino acids), but retain vCD30 activity as described herein.

A polypeptide or polypeptide fragment of the present invention may show one or more of the following properties; immunological cross-reactivity with an antibody reactive with a polypeptide for which the sequence is given in FIG. 1(*a*); sharing an epitope with a polypeptide for which the amino acid sequence is shown in FIG. 1(*a*)(as determined for example by immunological cross-reactivity between the two polypeptides); a biological activity which is inhibited by an antibody raised against a polypeptide having a sequence shown in FIG. 1(*a*).

Preferred polypeptides or fragments have vCD30 activity. A polypeptide which has vCD30 activity may have one or more of the following properties: binding to CD30 Ligand; inducing signalling in cells expressing CD30L; inhibiting the binding of CD30 to CD30L; inhibiting signalling in cells expressing CD30; modulating the immune response.

Modulating the immune response may include, for example, inhibiting type 1 cytokine responses and downregulating cytotoxic T cell and/or natural killer cell responses.

Preferred vCD30 polypeptides are poxvirus vCD30 polypeptides, for example Ectromelia virus vCD30 polypeptide.

Where additional amino acids are included in a polypeptide, is these may be heterologous or foreign to the vCD30 sequence.

For example, a vCD30 polypeptide may be included within a fusion protein (which may, for example consist of more than 111 amino acids) in which the vCD30 sequence is fused to a non-EV, non-poxviral or non-viral sequence (i.e. a heterologous or foreign sequence). Non-viral sequence may include a polypeptide or protein domain, for example, an immunoglobulin binding domain or other functional moiety.

Unrelated viral sequences may be fused to the vCD30 polypeptide sequence, for example one or more additional virally encoded C terminal amino acid residues not encoded by the vCD30 gene (gene E13 of ectromelia strain Naval). These one or more residues may comprise, for example, an extended C terminal domain. For example, the vCD30 polypeptide may be fused to the polypeptide encoded by the E12 gene of ectromelia strain Naval.

Also encompassed within the scope of the present invention are functional mimetics of vCD30 polypeptide (including fragments, alleles, mutants, derivatives and variants thereof). The term "functional mimetic" means a substance which may not contain an active portion of the relevant amino acid sequence, and probably is not a peptide at all, but which retains in qualitative terms the biological activity of natural vCD30 polypeptide. The design and screening of candidate mimetics is described in detail below.

A vCD30 polypeptide may be in isolated and/or purified form, free or substantially free of material with which it is naturally associated, such as other viral or mammalian polypeptides, or (for example if produced by expression in a prokaryotic cell) lacking in native glycosylation, e.g. unglycosylated. A polypeptide may be provided free or substantially free of other polypeptides.

The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below, for example to modulate immune responses in an individual.

Another aspect of the present invention provides an isolated nucleic acid molecule comprising or consisting of a nucleic acid sequence encoding a vCD30 polypeptide as described above.

The coding sequence may be the nucleotide sequence shown in FIG. 2(*a*) 2(*b*) or 2(*c*) or it may be a mutant, variant, derivative or allele of the sequence shown. The sequence may differ from that shown by a change which is one or more of addition, insertion, deletion and substitution of one or more nucleotides of the sequence shown.

Changes to a nucleotide sequence may result in an amino acid change at the protein level, or not, as determined by the genetic code.

Thus, nucleic acid according to the present invention may comprise or consist of a sequence different from the sequence shown in FIG. 2(*a*) 2(*b*) or 2(*c*), yet encode a polypeptide with the same amino acid sequence. On the other hand, the encoded polypeptide may have an amino acid sequence which differs by one or more amino acid residues from an amino acid sequence shown in FIG. 1(*a*). Nucleic acid may thus encode a polypeptide which is an amino acid sequence mutant, variant, derivative or allele of a sequence shown in FIG. 1(*a*). Such polypeptides are discussed above.

Another aspect of the present invention provides isolated nucleic acid that hybridises with the nucleic acid sequence of FIG. 2(*a*) 2(*b*) or 2(*c*) under stringent conditions. Suitable conditions include, e.g. for detection of sequences that are about 80–90% identical, hybridisation overnight at 42° C. in 0.25M $Na_2HPO_4$, pH 7.2, 6.5% SDS, 10% dextran sulphate and a final wash at 55° C. in 0.1×SSC, 0.1% SDS. For detection of sequences that are greater than about 90% identical, suitable conditions include hybridisation overnight at 65° C. in 0.25M $Na_2HPO_4$, pH 7.2, 6.5% SDS, 10% dextran sulphate and a final wash at 60° C. in 0.1×SSC, 0.1% SDS. Preferably such a nucleic acid encodes a CD30 polypeptide as described above.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA.

The coding sequence shown herein is a DNA sequence. Where nucleic acid according to the invention includes RNA, reference to the sequence shown should be construed as encompassing reference to the RNA equivalent, with U substituted for T.

Nucleic acid as described herein may be operably linked to a heterologous i.e. non-EV, non-poxviral or non-viral regulatory element.

Nucleic acid may be provided as part of a replicable vector. A replicable vector comprising nucleic acid as set out above may include an expression vector from which the encoded polypeptide can be expressed under appropriate conditions.

An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as *E. coli.*

An expression vector may comprise a nucleic acid as described above operably linked to a regulatory element. Suitable regulatory elements include heterogeneous regulatory elements (for example, a non-EV, non-poxviral or non-viral regulatory element). Vectors may be in an isolated form or contained within a host cell.

Nucleic acid encoding a vCD30 polypeptide is obtainable from samples comprising poxvirus DNA, for example genomic isolates of poxvirus infected cells, in particular EV or CPV infected cells, using one or more oligonucleotide probes or primers designed to hybridise with one or more fragments of the nucleic acid sequence shown in FIG. 2(*a*) 2(*b*) or 2(*c*). In particular, fragments of relatively rare sequence may be used based on codon usage or statistical analysis.

A primer designed to hybridise with a part of the nucleic acid sequence shown in FIG. 2(*a*) 2(*b*) or 2(*c*) may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with a sequence shown and a primer which hybridises to the oligonucleotide linker.

Nucleic acid isolated and/or purified from one or more poxvirus samples, for example poxvirus infected cells (e.g. mouse cells) or isolates or a nucleic acid library derived from nucleic acid isolated and/or purified from these cells (e.g. a cDNA library derived from mRNA isolated from the cells), may be probed under conditions for selective hybridisation and/or subjected to a specific nucleic acid amplification reaction such as the polymerase chain reaction (PCR) (reviewed for instance in "PCR protocols; A is Guide to Methods and Applications", Eds. Innis et al, 1990, Academic Press, New York, Mullis et al, Cold Spring Harbor Symp. Quant. Biol., 51:263, (1987), Ehrlich (ed), PCR technology, Stockton Press, NY, 1989, and Ehrlich et al, Science, 252: 1643–1650, (1991)). PCR comprises steps of denaturation of template nucleic acid (if double-stranded), annealing of primer to target, and polymerisation. The nucleic acid probed or used as template in the amplification reaction may be genomic DNA, cDNA or RNA. Other specific nucleic acid amplification techniques include strand displacement activation, the QB replicase system, the repair chain reaction, the ligase chain reaction and ligation activated transcription. For convenience, and because it is generally preferred, the term PCR is used herein in contexts where other nucleic acid amplification techniques may be applied by those skilled in the art. Unless the context requires otherwise, reference to PCR should be taken to cover use of any suitable nucleic amplification reaction available in the art.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RN'ase cleavage and allele specific oligonucleotide probing. Probing may employ the standard Southern blotting technique. For instance, DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments' on the filter and binding determined. DNA for probing may be prepared from RNA preparations from cells.

Preliminary experiments may be performed by hybridising, under low stringency conditions, various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on. On the basis of amino acid sequence information, oligonucleotide probes or primers may be designed, taking into account the degeneracy of the genetic code, and, where appropriate, codon usage of the organism from the candidate nucleic acid is derived. An oligonucleotide for use in nucleic acid amplification may have about 10 or fewer codons (e.g. 6, 7 or 8), i.e. be about 30 or fewer nucleotides in length (e.g. 18, 21 or 24). Generally specific primers are upwards of 14 nucleotides in length, but need not be than 18–20. Those skilled in the art are well versed in the design of primers for use processes such as PCR. Various techniques for synthesizing oligonucleotide primers are well known in the art, including phosphotriester and phosphodiester synthesis methods.

A further aspect of the present invention provides an oligonucleotide or polynucleotide fragment of the nucleotide sequence shown in FIG. 2(*a*) 2(b) or 2(c), or a complementary sequence, in particular for use in a method of obtaining and/or screening nucleic acid.

Some preferred oligonucleotides have a sequence shown in FIG. 2(*a*), 2(*b*) or 2(*c*), or a sequence which differs from any of the sequences shown by addition, substitution, insertion or deletion of one or more nucleotides, but preferably without abolition of ability to hybridise selectively with nucleic acid as described above, that is wherein the degree of similarity of the oligonucleotide or polynucleotide with one of the sequences given is sufficiently high.

Nucleic acids encoding CD30 polypeptides, including vCD30 polypeptides, may be used in methods of gene therapy, for instance in treatment of individuals with the aim of preventing or curing (wholly or partially) inflammatory conditions or other diseases. This may ease one or more symptoms of the disease. This is discussed below.

CD30 polypeptides may be generated wholly or partly by chemical synthesis or may be expressed recombinantly i.e. by expression from encoding nucleic acid. The skilled person can use the techniques described herein and others well known in the art to produce large amounts of polypeptides.

Peptides and short polypeptides, in particular, may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

A convenient way of producing a CD30 polypeptide is to express nucleic acid encoding it, by use of the nucleic acid in an expression system. Accordingly, the present invention also encompasses a method of making a polypeptide (as disclosed), the method including expression from nucleic acid encoding the polypeptide. This may conveniently be achieved by growing a host cell in culture, containing such a vector, under appropriate conditions which cause or allow expression of the polypeptide. Polypeptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli.*

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a host cell may contain nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A method for introducing the nucleic acid into a host cell may (particularly for in vitro introduction) be generally referred to without limitation as "transformation", and may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium.

Following production by expression, a polypeptide may be isolated and/or purified from the host cell and/or culture medium, as the case may be, and subsequently used as desired, e.g. formulated into a composition which may include one or more additional components, such as a pharmaceutical composition which includes one or more pharmaceutically acceptable excipients, vehicles or carriers (e.g. see below).

A method of producing a vCD30 polypeptide may comprise; causing or allowing expression from a nucleic acid as described herein to produce the encoded polypeptide and; purifying the polypeptide.

The polypeptide may be tested for vCD30 activity. For example, polypeptides may be tested for the inhibition of CD30 signalling in CD30 expressing cells and/or the promotion of CD30L signalling in CD30L expressing cells.

Instead of, or as well as, being used for the production of a polypeptide encoded by a transgene, host cells may be used as a nucleic acid factory to replicate the nucleic acid of interest in order to generate large amounts of it. Multiple copies of nucleic acid of interest may be made within a cell when coupled to an amplifiable gene such as dihyrofolate reductase (DHFR), as is well known. Host cells transformed with nucleic acid of interest, or which are descended from host cells into which nucleic acid was introduced, may be cultured under suitable conditions, e.g. in a fermentor, taken from the culture and subjected to processing to purify the nucleic acid. Following purification, the nucleic acid or one or more fragments thereof may be used as desired.

Non-peptide "small molecules" are often preferred for many in vivo pharmaceutical uses. Accordingly, a mimetic or mimick of the substance (particularly if a peptide) may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The invention thus extends to a mimetic, dervative or analogue of a vCD30 polypeptide as described herein, which may, for example be useful in a method of treatment of the human or animal body.

The present invention extends in various aspects not only to a vCD30 polypeptide as described above, but also to a vCD30 polypeptide, for use in a method of treatment of the human or animal body, and a vCD30 polypeptide for use in method of treatment of an inflammatory disorder.

Also encompassed by the present invention are a pharmaceutical composition, medicament, drug or other composition which comprises a vCD30 polypeptide, a method comprising administration of such a composition to a patient, e.g. for treatment (which may include preventative treatment) of an inflammatory disorder, use of a vCD30 polypeptide in the manufacture of a medicament for administration, e.g. for treatment of a inflammatory disorder, and a method of making a pharmaceutical composition comprising admixing a vCD30 polypeptide with a pharmaceutically acceptable excipient, vehicle or carrier, and optionally other ingredients. Such a composition may be for use in treating an inflammatory disorder.

Using the viral homologue vCD30, the present inventors, have shown, for the first time, the role of mammalian CD30 in modulating Th1 immune responses.

The present invention also provides a CD30 polypeptide, including a viral or mammalian (e.g. human) CD30 polypeptide for use in method of treatment of a Th1 mediated inflammatory disorder.

Preferably, a CD30 polypeptide binds to CD30L and promotes or stimulates intracellular signalling in CD30L expressing cells and/or blocks CD30 binding with CD30L, thereby inhibiting intracellular signalling in cells expressing CD30.

Other aspects of the present invention provide a pharmaceutical composition, medicament, drug or other composition for use in treating a Th1 mediated inflammatory disorder, which comprises a CD30 polypeptide, a method comprising administration of such a composition to a patient, e.g. for treatment (which may include preventative treatment) of an Th1 mediated inflammatory disorder, use of a CD30 polypeptide in the manufacture of a medicament for administration, e.g. for treatment of a Th1 mediated inflammatory disorder, and a method of making a pharmaceutical composition comprising admixing a CD30 polypeptide with a pharmaceutically acceptable excipient, vehicle or carrier, and optionally other ingredients. Such a composition may be for use in treating a Th1 mediated inflammatory disorder.

A CD30 polypeptide for use in accordance with these aspects of the present invention may be a mammalian, more preferably a human CD30 polypeptide and may, for example, have a sequence shown in FIG. 1 or may be a variant, allele, mutant of derivative thereof or a fragment of any of these, as described above. Such a CD30 polypeptide may be encoded by a nucleic acid sequence shown in FIG. 2.

An inflammatory disorder as described herein may include a Th1 mediated inflammatory disorder, i.e. a disorder in which Th1 responses occur, either predominantly or partially. Examples of Th1 mediated inflammatory disorders include type 1 cytokine mediated inflammatory disorders such as autoimmune diabetes, autoimmune disease, rheumatoid arthritis, systemic lupus erythematous, progressive systemic sclerosis, multiple sclerosis and ulcerative colitis.

Whether it is a polypeptide, peptide, nucleic acid molecule, small molecule or other pharmaceutically useful compound that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated. Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

Instead of administering an agent directly, it may be produced in target cells by expression from an encoding gene introduced into the cells, e.g. in a viral vector (see below). The vector may be targeted to the specific cells to be treated, or it may contain regulatory elements which are switched on more or less selectively by the target cells. Viral vectors may be targeted using specific binding molecules, such as a sugar, glycolipid or protein such as an antibody or binding fragment thereof. Nucleic acid may be targeted by means of linkage to a protein ligand (such as an antibody or binding fragment thereof) via polylysine, with the ligand being specific for a receptor present on the surface of the target cells.

Nucleic acid according to the present invention, e.g. encoding a biologically active CD30 polypeptide, may be used in a method of treatment of a patient with the aim of treating and/or preventing one or more symptoms of an inflammatory disorder.

Vectors such as viral vectors have been used to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see e.g. U.S. Pat. No. 5,252,479 and WO 93/07282. In particular, a number of viruses have been used as gene transfer vectors, including adenovirus, papovaviruses, such as SV40, vaccinia virus, herpesviruses, including HSV and EBV, and retroviruses, including gibbon ape leukaemia virus, Rous Sarcoma Virus, Venezualian equine enchephalitis virus, Moloney murine leukaemia virus and murine mammary tumourvirus. Many gene therapy protocols in the prior art have used disabled murine retroviruses.

Disabled virus vectors are produced in helper cell lines in which genes required for production of infectious viral particles are expressed. Helper cell lines are generally missing a sequence which is recognised by the mechanism which packages the viral genome and produce virions which contain no nucleic acid. A viral vector which contains an intact packaging signal along with the gene or other sequence to be delivered (e.g. encoding the vCD30 polypeptide) is packaged in the helper cells into infectious virion particles, which may then be used for the gene delivery.

Other known methods of introducing nucleic acid into cells include electroporation, calcium phosphate co-precipitation, mechanical techniques such as microinjection, transfer mediated by liposomes and direct DNA uptake and receptor-mediated DNA transfer. Liposomes can encapsulate RNA, DNA and virions for delivery to cells. Depending on factors such as pH, ionic strength and divalent cations being present, the composition of liposomes may be tailored for targeting of particular cells or tissues. Liposomes include phospholipids and may include lipids and steroids and the composition of each such component may be altered. Targeting of liposomes may also be achieved using a specific binding pair member such as an antibody or binding fragment thereof, a sugar or a glycolipid.

The aim of therapy using nucleic acid encoding a CD30 polypeptide, for example a vCD30 polypeptide, is to express the expression product of the nucleic acid in cells to reduce the binding of CD30 and CD30L and/or induce CD30L signalling and thereby to inhibit Th1 mediated inflammation. Such treatment may be therapeutic or prophylactic, particularly in the treatment of individuals known through screening or testing to have, or be at risk of having, an inflammatory disorder.

Various further aspects and embodiments of the present invention will be apparent to those skilled in the art in view of the present disclosure. All documents mentioned in this specification are incorporated herein by reference in their entirety.

Certain aspects and embodiments of the invention will now be illustrated by way of example and with reference to the figures described below.

FIG. 1(*a*) shows a pairwise alignment of the amino acid sequence of vCD30 in three distinct orthopoxviruses (SEQ ID NO: 1; SEQ ID NO: 2; SEQ ID NO: 3) and FIG. 1(*b*) shows a pairwise alignment of the amino acid sequence of human (SEQ ID NO: 4), mouse (SEQ ID NO: 5) and viral CD30 (SEQ ID NO: 1). Dark shadows represent differences (a) or similarities (b). Grey boxes represent regions of high similarity. Dots and stars indicate deletions and stop codons, respectively. The predicted signal peptide (SP) and transmembrane domain (TM) are indicated. The accession numbers of the sequences are: Y11842 (CPV-GRI90 vCD30), M83554 (human CD30) and U25416 (mouse CD30).

FIG. 2 shows the nucleotide sequences of the vCD30 polypeptides shown in FIG. 1; CPV GRI90 (a) (SEQ ID NO: 6), EV Hampstead (b) (SEQ ID NO: 7) and EV Naval (c) vCD30 (SEQ ID NO: 8), and human (d) (SEQ ID NO: 9) and mouse (e) CD30 (SEQ ID NO: 10).

Figure 4:
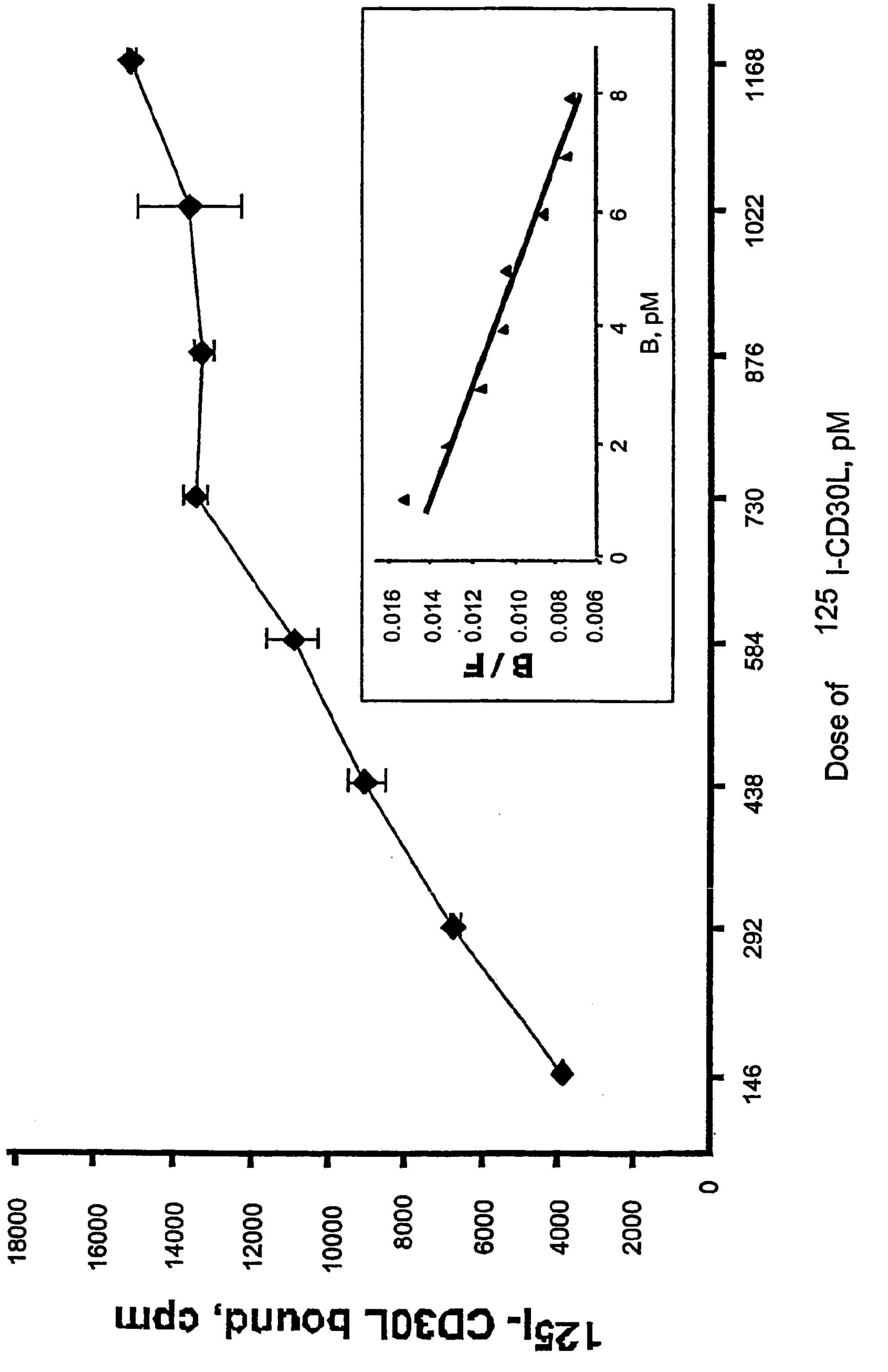

FIG. 4 shows the affinity of vCD30 for mouse CD30L. Data has been converted to the Scatchard co-ordinate system and analyzed with the LIGAND software. Specific $^{125}$I-CD30L binding of duplicate samples (mean±SD) is shown.

FIG. 5 shows CD30L binding activity and kinetics of production of the natural EV vCD30. FIG. 5(*a*) shows EV soluble CD30L binding activity. FIG. 5(*b*) shows BSC-I cells mock-infected or infected with EV strain Hampstead, in the absence or presence of AraC. The background radioactivity corresponding to the binding medium has been subtracted. Specific $^{125}$I-CD30L binding of duplicate samples (mean±SD) is shown.

Figure 6:
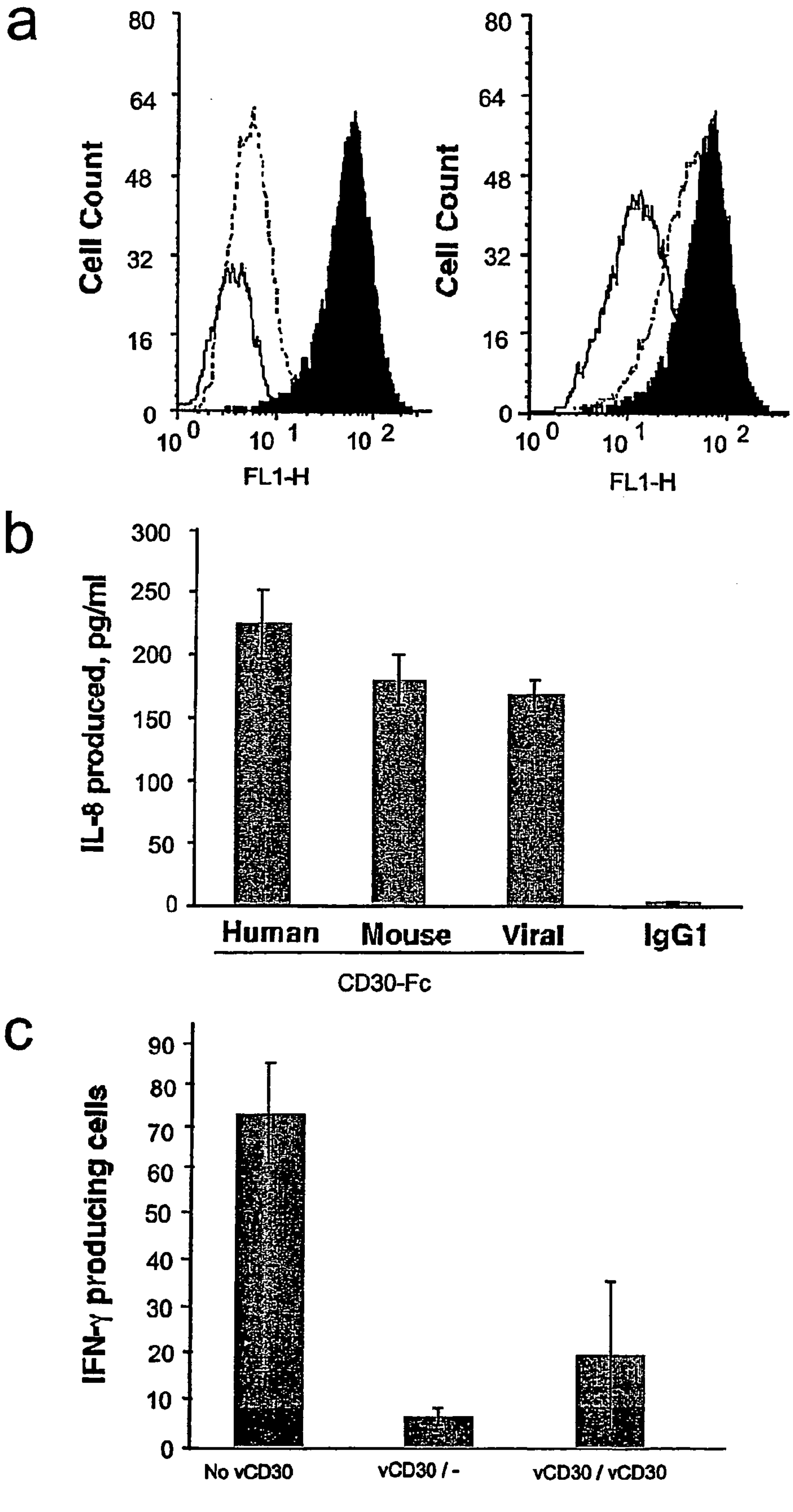

FIG. 6 shows biological activities of vCD30. FIG. 6(*a*) shows blockade of binding of soluble recombinant CD30L to CD30 expressed at the cell membrane. The profile of unstained cells (dashed line, left panel) and of cells stained in the absence of CD30L (solid line, left panel) is also shown. FIG. 6(*b*) shows IL-8 production by neutrophils induced by human, mouse or viral CD30-Fc. The figure shows a representative experiment of three done with neutrophils from different donors. FIG. 6(*c*) shows the role of vCD30 in in vitro T cell responses. The result of duplicate samples (mean±SD) is shown. “vCD30/−” denotes vCD30 added only in the priming phase and “vCD30/vCD30” denotes vCD30 added in both phases.

Figure 7:
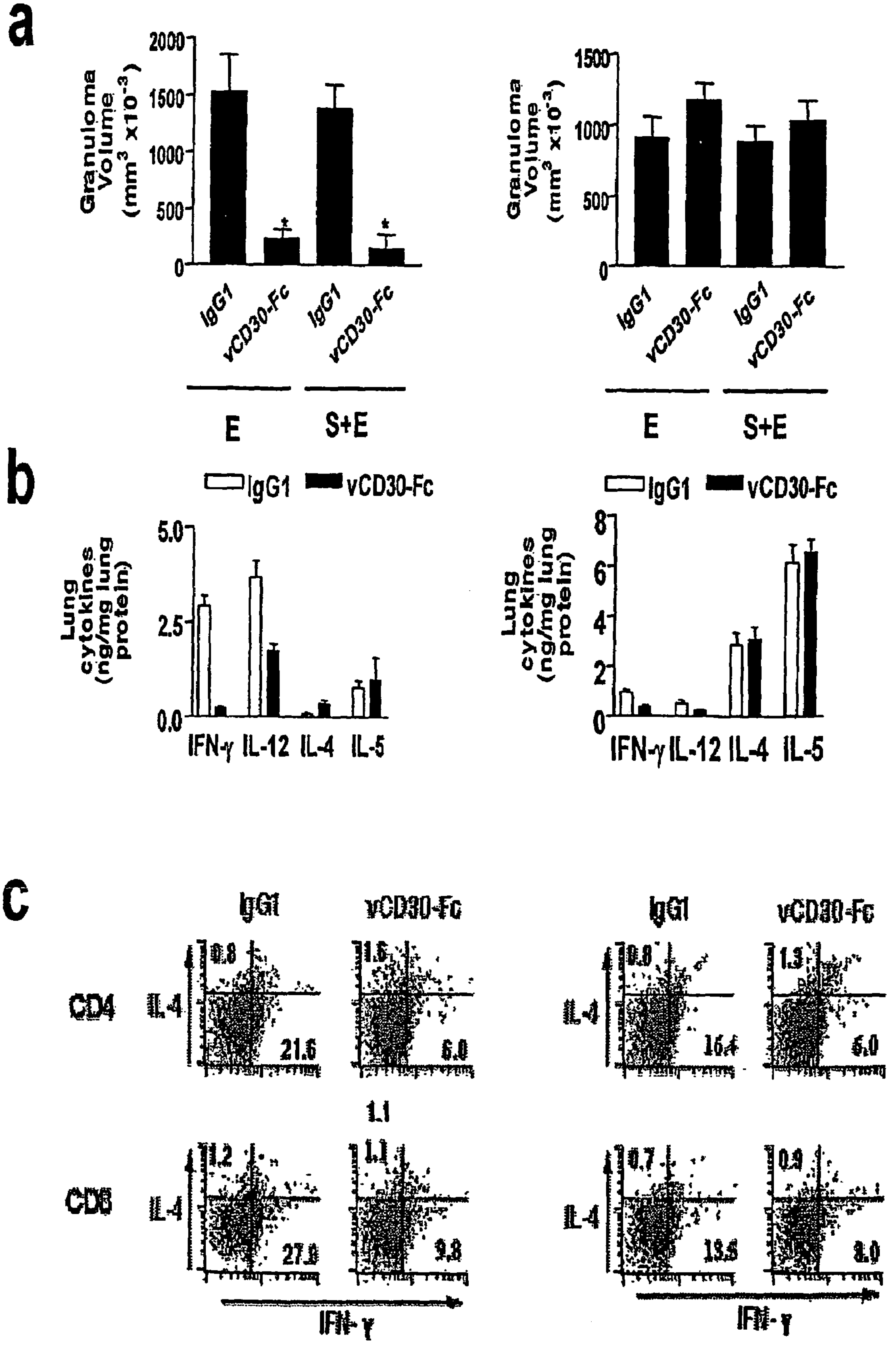

FIG. 7 shows the role of vCD30 during in vivo type 1 or type 2 cytokine-mediated pulmonary inflammation. FIG. 7(*a*) shows quantification of the granuloma volume (mean±SD) from 4–5 mice per group. FIG. 7(B) shows that vCD30-Fc treatment reduced lung tissue IFN-γ and IL-12 in type 1-sensitized mice. FIG. 7(*c*) shows intracellular detection of alterations in the frequencies of IFN-γ and IL-4 producing CD4$^+$ and CD8$^+$ T cells in type 1- or type 2-sensitized mice. Data in quadrants representative the percentage of positively stained cells. All data are representative from 2 separate experiments (n=4–5 mice per group). Cytokine and FACS data presented are from mice treated 4 times with vCD30-Fc. Comparable data was obtained in 2 separate experiments when mice were only treated 2 times.

EXPERIMENTAL

Material and Methods

Reagents

Recombinant mouse CD30L ($ED_{50}$=50–150 μg/ml), human CD30 ($ED_{50}$=0.03–0.1 μg/ml) and mouse CD30 ($ED_{50}$=0.03–0.1 μg/ml) were from by R&D Systems. The Iodine-125 (103.7 mCi/ml) and iodogen reagent used to radioiodinate mouse CD30L were purchased from Amersham and Pierce, respectively. The protein A-coated FlashPlates used for binding and affinity studies were from PerkinElmer Life Sciences. The mouse mAb specific for the histidine tag and the FITC-conjugated goat anti-mouse immunoglobulins used in flow cytometry were from Clontech and DAKO, respectively. *Mycobacteria tuberculosis* whole cell lysates (H37Rv strain) and PPD were obtained from Mycos Research, USA. Schistosome eggs and soluble egg antigens (SEA) were prepared as described (Fallon, P. G. et al *Eur. J. Immunol.* 28, 1408–1416 (1998)).

Cells, Viruses and Viral DNA Preparations

The growth of BSC-I, TK$^-$143B and K562 cells and the sources of VV WR strain and EV isolates Hampstead and Naval have been described (Smith and Alcami (2000) supra). W and EV were propagated in BSC-I cells and viral genomic DNA prepared as described (Esposito, J. et al *J. Virol. Methods* 2, 175–179 (1981)). The growth of *Autographa californica* nuclear polyhedrosis virus (AcNPV) in *Spodoptera frugiperda* (Sf) 21 insect cells has been described (Alcami, A. et al *J. Gen. Virol.* 80, 949–959 (1999). Tn5 B1–4 (Hi5) insect cells were cultured in EX-CELL serum free medium (European Collection of Cell Cultures).

DNA Sequencing

Specific oligonucleotides, CD30-1 (5' GTTCTGGATACATGCACAAAG 3'; SEQ ID NO: 11) and CD30-2 (5' GGAGGATAATCATTTGCAAACG 3'; SEQ ID NO: 12), were designed based on the sequence of CPV strain GRI90 ORF D13L (Shchelkunov, S. N. et al. *Virology* 243, 432–460 (1998)) and used to amplify by PCR, using Taq DNA polymerase, the cognate genes from viral DNA preparations from VV WR and EV Hampstead and Naval. PCR products were sequenced by the DNA Sequencing Service of the Department of Biochemistry (Cambridge University). The sequence data were analysed using Genetics Computer Group (GCG) computer programs (Genetics Computer Group (Wisconsin, USA, 1994)).

Construction of Recombinant Baculovirus Expressing the EV-Hampstead vCD30 Gene The EV-Hampstead vCD30 gene was amplified by PCR using Pfu DNA polymerase, virus DNA as template and oligonucleotides, CD30-3 (5'CGCAAGCTTGGATCCAT- GAAGATGAATACTA TCTTTTTATC 3'; SEQ ID NO: 13) and CD30-4 (5'CGCGCGGCCGCTGATGAGTATTTATGATAACAAAG 3'; SEQ ID NO: 14), corresponding to the 5' and 3' ends of the ORF and providing HindIII/BamHI and NotI sites, respectively. The resultant product was cloned into HindIII and NotI-digested pBac1 (Gibco), creating plasmid pMS2 (EV Hampstead vCD30). The DNA sequence of the insert was confirmed not to contain mutations. The Fc fragment of the human IgG1 was subcloned into NotI/SphI sites of pMS2, creating plasmid pMS18 (EV Hampstead vCD30-Fc). Recombinant baculovirus was produced as described (Alcami et al (1999) supra), and termed AcCD30-Fc (EV Hampstead vCD30-Fc, AcMS 18).

Purification of the Baculovirus Recombinant vcd30-Fc Protein

Hi5 cultures were infected with AcCD30-Fc at 10 pfu/cell and supernatants were harvested 3 to 4 days later, when full infection was observed. The recombinant vCD30-Fc was subsequently purified using a Protein A-HiTrap column (Amersham). The purified protein was then-analyzed by SDS-PAGE in 12% acrylamide gels and stained with Coomassie blue. Protein concentration was determined using the Biorad protein assay reagent.

Construction of Recombinant VV Expressing the EV Hampstead vCD30 Gene

The EV Hampstead vCD30 gene was amplified by PCR with virus DNA as template, Pfu DNA polymerase and oligonucleotides CD30-3 and CD30-5 (5'CGCGGTACCTCATGATGAGTATTT ATGATAACAAAG 3'; SEQ ID NO: 15) containing KpnI restriction site. The DNA fragment was cloned into BamHI and KpnI-digested pMJ601 (Davison, A. J. & Moss, B. *Nucleic Acids Res.* 18, 4285–4286 (1990), creating plasmid pMS12 (EV Hampstead vCD30). The DNA sequence of the insert was confirmed not to contain mutations. The recombinant VV was produced as described (Alcami et al (1999) supra) and termed VVCD30 (EV Hampstead vCD30, vMS12).

Metabolic Labelling of VVCD30 and Electrophoretic Analysis

BSC-I cells were infected with VV WR or VVCD30 at 10 pfu/cell. Cultures were pulse-labelled with 150 μCi/ml [$^{35}$S] methionine (Amersham; 1200 Ci/mmol) and 150 μCi/ml [$^{35}$S]cysteine (NEN; 600 Ci/mmol), in methionine- and cysteine-free medium in the absence of serum. Cells or media were dissociated in sample buffer and analyzed by SDS-PAGE in 12% acrylamide gels and fluorography with Amplify (Amersham).

Preparation of VV and EV Supernatants

BSC-I cells were mock-infected or infected with VV-WR, VVCD30, EV Hampstead, EV Naval at 10 pfu/cell in phenol red and serum-free medium and supernatants were harvested at 2 (for the VV infections) or 3 (for the EV and mock infections) days p.i. and prepared and inactivated as described (Alcami, A. et al *J. Immunol.* 160, 624–633 (1998)).

CD30L Binding Assay

Recombinant mouse CD30L was radioiodinated to a specific activity of $1\times10^6$ cpm/μg using the Iodogen method (Markwell, M. A. & Fox, C. F. *Biochemistry* 17, 4807–4817 (1978)). Approximately 150 pM of $^{125}$I-CD30L was incubated for 12 h with 5 ng of purified vCD30-Fc or recombinant mouse CD30 in a protein A-coated FlashPlate. The binding medium was phenol red-free-MEM, 0.1% BSA, 20 mM Hepes, pH 7.5. The amount of CD30L bound to the viral receptor was measured in a Packard Topcount microplate counter. Non-specific binding was determined by incubating $^{125}$I-CD30L with binding medium only. For the competition studies a 500-fold molar excess of cold mouse CD30L was added to the recombinant mouse or viral receptors prior to the addition of $^{125}$I-CD30L. To test the CD30 binding activity in supernatants of EV Hampstead and Naval, VV WR or VVCD30, 50 μl of supernatant equivalent to $1.5\times10^4$ cells were pre-incubated with $^{125}$I-CD30L, before addition to the recombinant mouse or viral receptors.

For the determination of the affinity constant of both mouse and viral CD30 to the CD30L, binding assays with increasing amounts of $^{125}$I-CD30L against a fixed amount of recombinant CD30 (2 and 0.5 ng of mouse or viral protein, respectively) were performed. The results were analyzed with the LIGAND software (Munson, P. J. & Rodbard, D. *Anal. Biochem.* 107; 220–239 (1980)).

For determination of membrane-bound activity of vCD30, BSC-I cells were mock-infected or infected with VV WR, WCD30, EV Hampstead at 10 pfu/cell. Twenty four h later human 125I-CD30L was added and bound $^{125}$I-CD30L determined by phthalate oil centrifugation (Alcami et al (1999) supra).

Kinetics of vCD30 Production During EV infection

BSC-I cells were mock-infected or infected with 10 pfu of EV Hampstead per cell, in the absence or presence of AraC (40 μg/ml), an inhibitor of DNA replication, and harvested at different times p.i. Supernatants were inactivated and the CD30 binding activity tested as described above. Total RNA was extracted by using the guanidine thiocyanate-based DNA/RNA Isolation kit (Promega) following the manufacturer's instructions. Total RNA (from $7\times10^4$ cells) was then analyzed by RT followed by PCR. RT was performed in presence of oligo$(dT)_{15}$ (Promega), RNAsin (Amersham) and AMV reverse transcriptase (Boerhinger-Manheim). The cDNA (2.5 μl of 40 μl) was amplified by PCR using Tag polymerase and oligonucleotides specific for vCD30, CD30-3 and CD30-4. DNA from BSC-I cells was included as a negative control.

Biological Activity of the vCD30

In Vitro Studies

Recombinant soluble mouse CD30L (1 μg/ml), pre-incubated with RPMI or a 25-fold excess of vCD30 or human IgG1 for 1.5 h at 4° C., was added to $1\times10^6$ K562 cells and incubated for 2 h at 4° C. After this period, cells were incubated for 40 min at 4° C. with a mouse mAb specific for the histidine tag (1 μg/ml in 0.1% BSA in PBS), that would recognize CD30L bound to the cell membrane. This antibody was subsequently developed with a FITC-labelled goat anti-mouse immunoglobulin antibody for 30 min at 4° C. Cells binding CD30L were then detected by FACS. Unstained cells and cells stained in the absence of CD30L were included as a control.

To test the ability of vCD30 to induce reverse signaling via membrane bound CD30L, $5\times10^4$ freshly isolated human neutrophils were incubated in a volume of 100 μl for 5 h at 37° C., in 96 well plates pre-coated with 10 μg/ml of mouse, human or vCD30, human IgG1 or PBS, as described (Wiley et al (1996) supra). After this period supernatants were harvested and the production of IL-8 measured by ELISA (Diaclone).

To address the possible interference of vCD30 in the development of CTL responses, $4\times10^5$ freshly isolated splenocytes from Balb/c mice were mixed in 96 well plates with $2\times10^4$ L929 cells, in a final volume of 200 μl of RPMI, in the presence or absence of 10 μg/ml of vCD30-Fc or IgG1, supplemented with 10% FCS, sodium pyruvate and non-essential amino acids, for 5 days at 37° C., 5% $CO_2$. After this period, IL-2 (Roche) was added to a final concentration of 50 U/ml and the incubation held for other 2 days. Finally, cells were harvested and the viable cells counted by trypan blue exclusion. Activated splenocytes ($1\times10^5$) were mixed again with L929 ($1\times10^4$), in the presence or absence of 10 μg/ml of vCD30-Fc or IgG1, and the number of cells producing IFN-γ measured using a ELISPOT assay (R&D Systems).

In Vivo Studies

Type 1 and type 2 cytokine-dominated pulmonary granulomas were induced, respectively, by mycobacterial or *Schistosoma mansoni* egg antigens as described (Chensue, S. W. et al *J. Immunol.* 159, 3565–3573 (1997)). Female Balb/c mice were obtained from Harlan. vCD30-Fc or control IgG1 (Sigma) were injected i.p. (10 μg per injection) throughout sensitization and elicitation of bead granulomas, i.e. on days 0, 7, 14 and 16, or were injected only during elicitation of granulomas on days 14 and 16.

On day 0 mice were sensitized by i.p. injection of 20 μg *M. tuberculosis* whole cell lysates in Complete Freund's Adjuvant (type 1 cytokine sensitization) or 5,000 *S. mansoni* eggs (type 2 cytokine sensitization). 14 days later mice were injected i.v. with 5,000 Sepharose 4B beads covalently coupled with PPD or SEA. Mice were terminated 4 days after bead injection on day 18. The left lung lobe was snap-frozen and used for cytokine analysis and the remainder of the lung was fixed for histological studies.

The diameters of the granuloma surrounding at least 50 individual beads per mouse were measured. Group mean granuloma volumes from 4–5 mice per group are presented. Statistical differences between groups were determined using Student's t-test.

Lung tissue cytokines were determined as reported using previously described ELISA protocols (Fallon, P. G. & Dunne, D. W. *J. Immuno.* 162, 4122–4132 (1999)). Control naïve mouse lungs were processed to determine basal lung cytokine levels. Data was expressed as ng cytokine per mg lung protein. The spleen and draining mediastinal lymph nodes were removed from mice on the day of termination and used for cell culture and intracellular cytokine staining (Fallon et al (1998) supra).

In brief, spleen cell suspensions were cultured for 6 h in media-alone or in the presence of 6 μg/ml Concanavalin A (Sigma) and Brefeldin A (10 μg/ml; Sigma) added for the last 4 h. All intracellular detection reagents were from Caltag Laboratories (CA, USA). Cells were surface stained with Tri-Color-conjugated anti-CD4 or CD8 mabs and following cell permeabilization cells were incubated with a FITC-conjugated anti-IFN-γ-mAb, PE-conjugated anti-IL-4 mAb or FITC- or PE-conjugated isotype control mAbs. For FACS analysis $CD4^+$ or $CD8^+$ lymphocytes were gated and quadrants were set using isotype control mAbs. The frequencies of IFN-γ and IL-4 stained cells are expressed as percentages.

Results

Identification of a Novel Member of the TNFR Superfamily Encoded by EV

Figure 1:
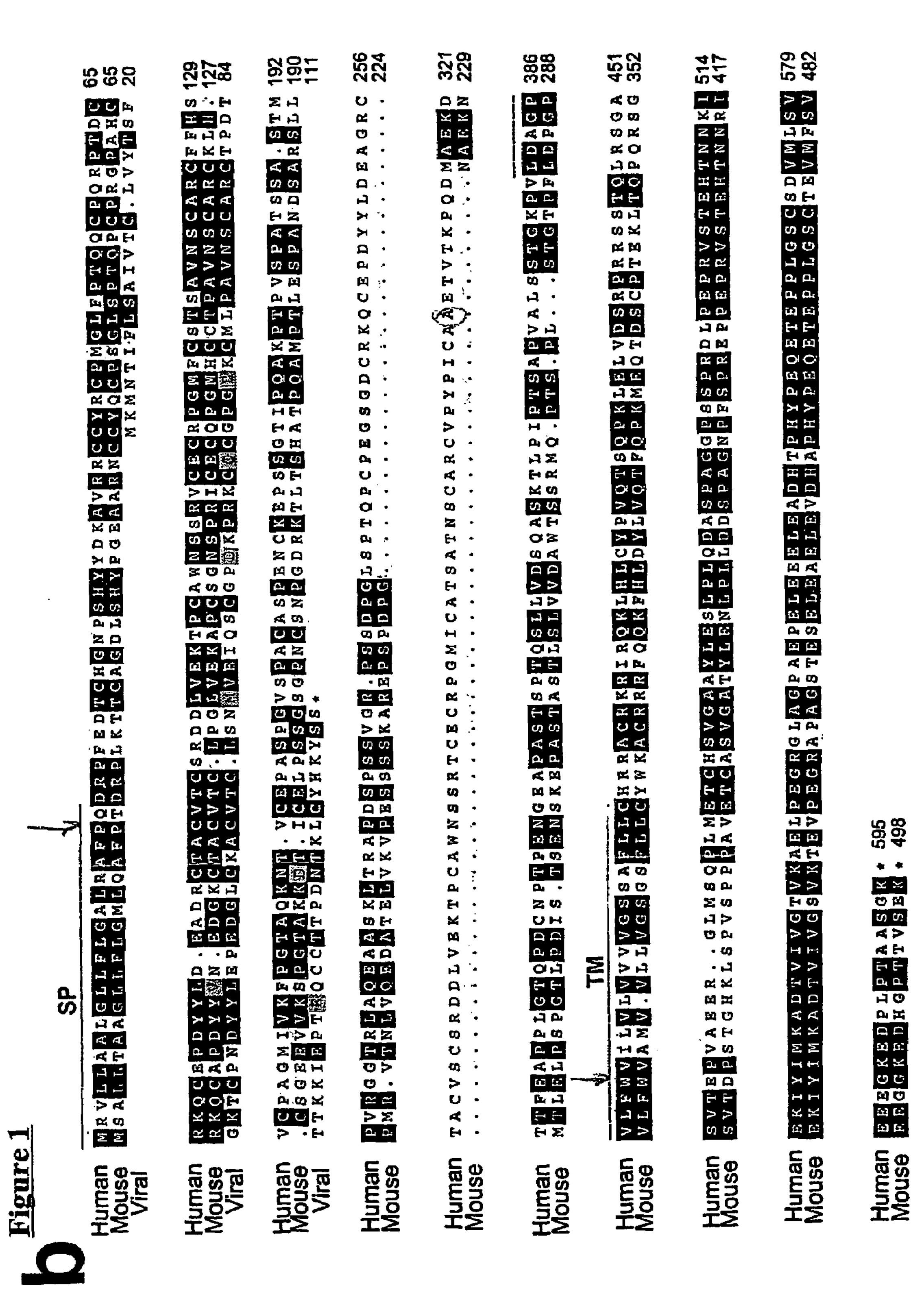

Analysis of the CPV strain GR1 90 sequence (Shchelkunov, S. N. et al. (1998) supra) revealed the presence of an ORF (D13L) with sequence similarity to host CD30, a TNFR superfamily member, and distinct from the previously identified poxvirus TNFRs (CrmB, C, D and E). PCR and sequence analysis of the cognate gene in EV isolates Hampstead and Naval showed the existence of an intact viral (v)CD30 gene (FIG. 1*a*). The predicted viral molecule lacked N-glycosylation sites, was considerably smaller (12 kDa) than the mouse or human counterparts (52 and 120 kDa, respectively), and aligned with CRDs found in the extracellular domain of the host CD30, with some motifs highly conserved (FIG. 1*b*). Interestingly, vCD30 showed a higher similarity to mouse (38%) than to human (32%) CD30. The existence of a signal peptide and the lack of transmembrane domain suggested that vCD30 may act as a is soluble decoy receptor for host CD30L.

Characterisation of the vCD30 Protein

A recombinant VV Western Reserve (WR) expressing the EV vCD30 under a strong promoter was constructed. PCR analysis indicated the absence of the vCD30 gene in W WR.

BSC-I cells were infected with VV-WR or VVCD30 and pulse-labelled with [$^{35}$S]cysteine and [$^{35}$S]methionine from 4 to 8 h p.i. Proteins present in cells and media were analyzed by sodium dodecyl sulfate-polyacrylamide gel electrophoresis (SDS-PAGE) in the presence or absence of β-mercaptoethanol (βME) and visualized by fluorography.

This showed that vCD30 was efficiently secreted from infected cells as a 12-kDa protein.

In the absence of reducing agents, a major product of 45 kDa was observed that suggested vCD30 is secreted as a disulfide bound trimer. The EV vCD30 was also expressed in the baculovirus system fused to the Fc region of human IgG1. Hi5 insect cells were infected with the recombinant baculovirus expressing vCD30-Fc, harvested 3 days p.i. and the recombinant protein purified by affinity chromatography in a protein A sepharose column. The fractions containing the purified vCD30-Fc were then concentrated and analyzed by SDS-PAGE.

The molecular size of the recombinant product (vCD30-Fc) was consistent with vCD30 encoding a 12 kDa protein.

CD30L Binding Activity, Specificity and Affinity of vCD30.

CD30L binding activity was determined using a scintillation proximity assay.

Five ng of purified recombinant vCD30-Fc, or mouse CD30-Fc (moCD30-Fc) were incubated for 12 h with 150 pM of mouse $^{125}$I-CD30L, in the presence or absence of unlabelled CD30L, in protein A-coated FlashPlates (PerkinElmer Life Sciences), containing a thin layer of scintillant in the interior of each well. Recombinant CD30 proteins are immobilized by the Fc portion and bound 125I-CD30L induces a signal detectable in a scintillation counter. Free 125I-CD30L is not detected in this assay and its removal was therefore unnecessary.

Figure 3:
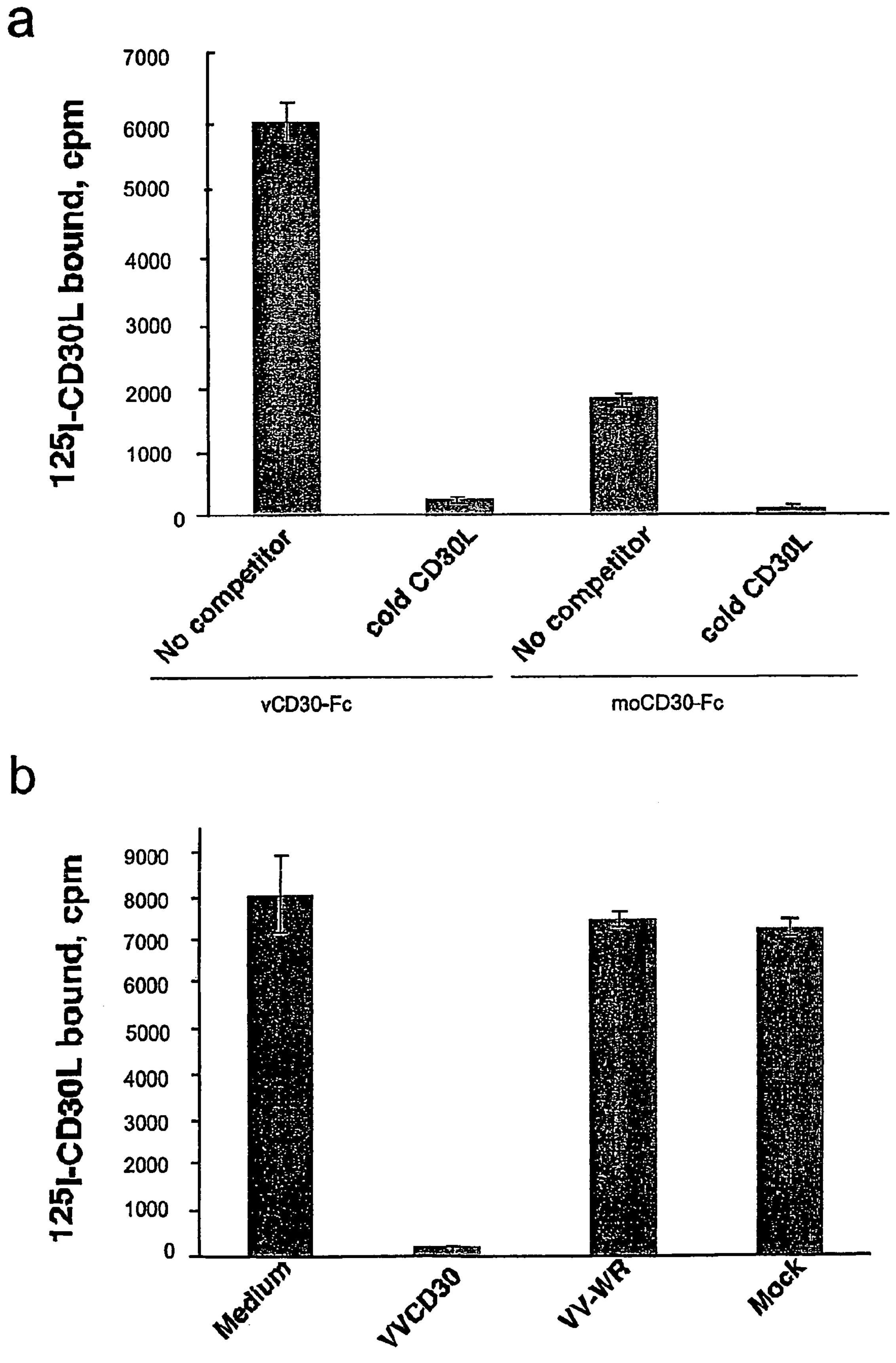
FIG. 3(*a*) shows CD30L binding activity of vCD30-Fc expressed from VVCD30 and FIG. 3(*b*) shows CD30L binding activity of recombinant vCD30 expressed from VVCD30. The background radioactivity in the absence of recombinant protein has been subtracted. $^{125}$I-CD30L binding of duplicate samples (mean±SD) is shown.

Both vCD30-Fc and moCD30-Fc specifically bound $^{125}$I-CD30L (FIG. 3*a*). Interestingly, the viral protein seemed to have a better binding capacity than the mouse counterpart.

The activity of the recombinant vCD30 expressed from W (VVCD30) was determined by measuring its ability to block the binding of $^{125}$I-CD30L to vCD30-Fc. 200 pM of mouse $^{125}$I-CD 30L, was incubated with supernatants (75 μl), equivalent to $1.5\times10^4$ cells, from cells uninfected or infected with VVCD30 or VV WR prior to its addition to vCD30-Fc (5 ng) in the FlashPlate binding assay. Only the VVCD30 supernatant blocked the binding of $^{125}$I-CD30L to the vCD30-Fc demonstrating that the protein expressed from the W recombinant is active (FIG. 3*b*).

TNF binding activity at the surface of cells infected with W strain Lister has been reported (Alcami et al (1999) supra). However, binding assays of $^{125}$I-CD30L to cells infected with VVCD30 failed to detect CD30L binding activity at the cell surface.

The binding affinity of mouse and viral CD30 for mouse CD30L was determined in binding assays using the protein A-coated FlashPlates with increased doses of labelled ligand. 0.5 ng of vCD30 was incubated in the protein A-coated FlashPlates with different amounts of mouse $^{125}$I-CD30L and the radioactivity bound determined in a Packard Topcount Microplate Counter. Scatchard analyses showed an affinity of 1±0.1 nM for vCD30 (FIG. 4).

The affinity determined for mouse CD30 was 1±0.3 nM, comparable to that determined by other methods for the interaction of human CD30 with mouse or human CD30L (2.5±0.3 nM) (Smith et al 1993 supra).

The EV-encoded CD30 is Expressed at Late Times p.i. and Binds CD30L

To investigate the binding activity of natural vCD30, supernatants from cells uninfected or infected with EV isolates Hampstead or Naval were tested in binding assays.

Mouse 125I-CD30L (200 pM) was pre-incubated with supernatant (equivalent to $1.5 \times 10^4$ cells) from BSC-I cells mock-infected or infected with EV strains Hampstead or Naval, and then incubated with 5 ng of vCD30-Fc in a protein A-coated FlashPlate. The binding of $^{125}$I-CD30L was determined in a Packard Topcount Microplate Counter. At 6 h p.i. (Early) or 24 h p.i. (Late) supernatants were harvested and an aliquot (equivalent to $5 \times 10^4$ cells) was tested for its ability to block the binding of 200 pM of $^{125}$I-CD30L to 5 ng of vCD30-Fc. Bound $^{125}$I-CD30L was determined as above.

The naturally produced EV protein efficiently blocked the binding of mouse $^{125}$II-CD30L to vCD30-Fc (FIG. 5*a*). Moreover, vCD30 was expressed at late times p.i., since supernatants prepared in the presence of cytosine arabinoside (AraC), an inhibitor of DNA replication that prevents expression of late viral proteins, did not show binding activity (FIG. 5*b*). Failure to detect by RT-PCR vCD30-specific transcripts in cell extracts at early times p.i., in the presence of AraC, confirmed this result.

Biological Activity of vCD30

The ability of vCD30 to block CD30L binding to cell surface receptors was investigated. We first screened by flow cytometry human and mouse cell lines for CD30 expression, using soluble recombinant mouse CD30L which cross-reacts with human receptors.

K562 cells were incubated with a 6× histidine-tagged CD30L and binding was detected with a mouse antibody specific for the histidine tag on the CD30L recombinant molecule followed by a FITC-goat anti mouse antibody (FIG. 6*a*: filled peak).

Staining profiles indicated that human monocyte K562 cells expressed high levels of CD30 (FIG. 6*a*). Addition of a 25-fold excess of vCD30-Fc (solid line, right panel FIG. 6*a*), but not of IgG1 (dashed line right panel: FIG. 6*a*), efficiently blocked CD30L binding to K562 cells.

As little as a 10-fold excess of vCD30-Fc was sufficient to interfere with the binding of CD30L to its cellular receptors.

In addition to blocking the CD30/CD30L interaction, vCD30 had the potential to bind CD30L expressed at the cell surface and to trigger intracellular-signals. Neutrophils constitutively express CD30L, but not CD30, and rapidly produce IL-8 when stimulated by CD30 (Wiley et a (1996) supra). We therefore analyzed the production of IL-8 by freshly isolated human neutrophils in response to immobilized human, mouse or viral CD30-Fc proteins or IgG1.

Freshly isolated neutrophils were incubated for 5 h in the presence of the indicated immobilized Fc fusion proteins or IgG1. Supernatants were harvested and assayed for IL-8 production by ELISA. IL-8 secretion of duplicate samples (mean±SD) is shown in FIG. 6*b*.

The viral homologue was observed to induce a response comparable to that of the mammalian receptors, whereas human IgG1 had no effect on IL-8 production.

Finally, we investigated the role of vCD30, and indirectly of the CD30/CD30L pair, in the development of T cell responses in vitro. We determined the influence of vCD30 on the activation of IFN-γ-producing cells in a mixed lymphocyte reaction (MLR).

Freshly isolated splenocytes from Balb/c mice were mixed with irradiated L929 cells in absence or presence of vCD30. Five days later IL-2 was added and the incubation held for other two days. After this priming phase, the viable cells were harvested and incubated with irradiated L929 for 20 h, in presence of vCD30. Cell activation was measured by their ability to produce IFNγ. The number of cells secreting IFNγ was assayed by ELISPOT.

As shown in FIG. 7*b*, vCD30 almost totally abrogated the production of IFN-γ by splenocytes from Balb/c mice exposed to L929 cells of different haplotype. The presence of vCD30 in the priming phase was sufficient to cause this effect. This result indicated the important role of the CD30/CD30L interaction in the establishment of T cell responses, particularly at early stages of activation. Moreover, the viral protein may be targeting this interaction to protect the virus against host T cell responses. The presence of IgG1 had no effect on the development of the T cell response.

Biological Role of vCD30 In Vivo.

To address the potential immunomodulatory activity of vCD30 in vivo, the effects of vCD30-Fc treatment on inflammation in a pulmonary granuloma model were investigated. In this model, type 1 and type 2 cytokine-mediated granulomas are induced in Balb/c mouse lungs by bead-immobilized mycobacterial purified protein derivative or *Schistosoma mansoni* egg antigens, respectively, as described above. Mice were treated with vCD30-Fc or control IgG1 during antigen sensitization and elicitation (4 treatments over 18 days), or only during elicitation (2 treatments over 4 days). The levels of IFN-γ, IL-12, IL-4 and IL-5 in lung tissue homogenates were tested in ELISA.

Photomicrographs of hematoxylin and eosin-stained sections of representative type 1 (lymphocytes, monocytes and neutrophils rich) or type 2 (eosinophil dominated) pulmonary granulomas surrounding antigen coated beads in mice treated with vCD30-Fc or IgG1 indicated that administration of vCD30-Fc to mice caused a significant impaired type 1 cytokine-mediated inflammatory response, with pulmonary granuloma size reduced >80% ($p<0.01$; Student's t-test) as compared to IgG1-treated mice. Significantly smaller type 1 granulomas were found in mice treated 2 or 4 times with vCD30 compared to IgG1 treated mice.

This effect was observed when vCD30 was administered throughout both the sensitization and elicitation response or only during elicitation (FIG. 7*a*). In contrast, type 2 cytokine-mediated pulmonary inflammation was not modified by vCD30 administration, with vCD30-Fc-treated mice having comparable, or marginally larger, granulomas than obtained in control animals. The composition of the cellular infiltrate surrounding the type 1 or type 2 granulomas was not altered by vCD30 treatment.

The effect of vCD30 on pulmonary cytokines responses was measured in lung tissue homogenates. Levels of type 1 or type 2 cytokines in the lungs of control IgG1-treated mice were biased in the respective type 1 (elevated IFN-γ and IL-12) or type 2 (IL-4 and IL-5)-mediated pulmonary inflammatory responses (FIG. 7*b*). vCD30 treatment of mice with type 1 granulomas caused a substantial reduction in lung IFN-γ and, albeit to a lesser degree, IL-12 levels (FIG. 6*c*), with no alterations in IL-4 and IL-5 levels. Cytokine levels in mice with type-2 granulomas were not altered by vCD30, although IFN-γ and IL-12 levels were lower in vCD30-treated mice. Changes in pulmonary type 1 cytokines levels occurred when vCD30 was administered throughout the experiment or only during elicitation.

These results demonstrate that the formation of type 1, but not type 2, cytokine-mediated pulmonary inflammation was impaired by vCD30 in vivo. To address whether the reduced IFN-γ production in vCD30-treated mice was associated with alterations in the production of type 1 (IFN-γ) or type 2 (IL-4) cytokines by T cells, we performed intracellular cytokine staining on $CD4^+$ or $CD8^+$ T cells from spleens. Cells from the spleens of type 1 granuloma-sensitized mice treated with vCD30 had 2–3 fold lower frequencies of both Th1 and Tc1 cells compared to control IgG1-treated mice (FIG. 7*c*). Similarly, vCD30 treatment also reduced the numbers of IFN-γ secreting T cells in type 2 granuloma-sensitized mice. These results support a preferential effect of vCD30 on type 1 T cells.

The identification and characterization of a homologue of mammalian CD30, designated vCD30, encoded by EV, is described herein. vCD30 is a new member of the TNFR superfamily that binds CD30L. Comparative studies in 10 other Ev isolates showed that all of them encode an active vCD30. The presence of an active vCD30 seems restricted to a few poxviruses. An intact vCD30 gene has been identified in EV isolates and CPV GRI-90, whereas it is not found in VV strain WR or in other 13 poxviruses, including three strains of VaV, whose complete genome has been sequenced and is available in public databases.

Amino acid sequence similarity of vCD30 with the human and mouse counterparts is confined to a region of the extracellular domain, since the viral protein lacks the transmembrane or cytoplasmic domains. The extracellular domain of human CD30 consists of a duplicate structure of three CRDs, whereas the mouse and viral counterparts only have the first cluster. This indicates direct involvement of the first CRDs in ligand binding, as shown for TNFR I (Marsters, S. A. et al *J. Biol. Chem.* 267, 5747–5750 (1992)). Moreover, conservation of some motifs in the three molecules, may point at specific residues involved in CD30L binding. Both mouse and human, CD30 can be proteolytically cleaved by a zinc metalloprotease to produce a soluble form (sCD30) that is larger than vCD30. The viral protein appears to retain the minimal structure necessary for efficient CD30L binding activity. The higher similarity of vCD30 to mouse CD30 is consistent with mice being the natural host for EV.

vCD30 is the fifth member of the TNFR superfamily identified in poxviruses and the only one that does not bind TNF, indicating a distinct role during viral infection. The sequence similarity between vCD30 and the other vTNFRs (CrmB, C, D and E) is confined to the CRDs. CrmB and CrmD show an extended C-terminal region with no sequence similarities in databases which is not required for TNF binding. Interestingly, the ORF downstream vCD30 in the EV strain Naval genome has similarity to the C-terminal extension found in some vTNFRs and no intergenic region is found. The ancestral vCD30 gene may have contained the C-terminal extension which has been lost in the gene presently found in EV.

vCD30 is a 12 kda protein secreted at late times during EV infection that binds CD30L with high affinity and inhibits its binding to cell surface CD30. This function of vCD30 is similar to that of the poxvirus soluble cytokine decoy receptors, including vTNFRs. However vCD30 has an additional unique property: it induces reverse signaling in cells expressing CD30L. Therefore, vCD30 may not be classified as a genuine decoy receptor and the mechanism of action of vCD30 may be totally different to that adopted by vTNFRs. Since no secreted form of CD30L has been identified to date, vCD30 may be acting at the cell surface, both mimicking signal transduction mediated by CD30 and inhibiting the effect of CD30L in cells expressing CD30. vCD30 is demonstrated to be a soluble molecule with no membrane-associated binding activity.

The expression of CD30 is associated with the activated status of T cells. In vitro, it has been mainly associated with a Th2/Th0 phenotype (Del Prete, G. et al. *Faseb J.* 9, 81–86 (1995)), although in vivo studies suggest that the relationship between $CD30^+$T cells and Th1 or Th2 profiles is very complex. Recent studies support a novel regulatory mechanism for CD30 in Th1 polarized responses such as rheumatoid arthritis (Gerli, R. et al. *Trends Immunol.* 22, 72–77 (2001)). Blockade of binding of CD30L to CD30 by the viral protein and/or the activation of CD30L by vCD30 is responsible for inhibition of IFN-γ production by activated splenocytes in MLR. The potent in viva inhibition of pulmonary granuloma formation by vCD30 in type 1, but not type 2, cytokine-sensitized mice supports a preferential role for CD30/CD30L in type 1 cytokine-mediated responses. Consistent with our in vitro data, a potential direct affect of vCD30 on type 1 T cells was shown by the diminished frequencies of IFN-γ producing T cells detected in vCD30-treated mice. These data support increasing evidence for a key role of CD30 in type 1 responses in vivo.

vCD30 treatment was effective in suppressing type 1 cytokine-mediated inflammation when administered either throughout the antigen sensitization and elicitation phase or only during elicitation. In the context of viral infection, this is compromising a protective anti-viral immune response, which is known to be Th1-like T cell mediated.

CD30 is also known to be expressed in activated B cells (Horie, R. & Watanabe, T (1998) supra) CD30L was found to be a potent mediator of mouse B cell growth and differentiation in vitro, although different results were found with human B cells. Therefore, vCD30 may also interfere with B cell responses to the virus. Finally, vCD30 may also modulate signaling between B and T cells, a process in which CD30 has been implicated. Pathogenesis studies of an EV lacking the vCD30 gene will provide further information on the role of CD30 in viral infections.

The finding of a virus-encoded CD30 homologue represents a novel immune evasion strategy and indicates a role of the CD30/CD30L system in anti-viral immune responses. Increased levels of sCD30 have been reported in pathological conditions and after infection with HIV, EBV, hepatitis virus B and C, measles virus and varicelia-zoster virus, but the biological significance is not known. Viral proteins have been optimized during virus-host co-evolution to become potent inhibitors of host immune responses. It is therefore possible that the biological properties of vCD30 differ from those of the host sCD30.

Characterization of viral immunomodulatory proteins may also shed light into the function of the host counterparts. By using vCD30, we demonstrate a role of CD30/CD30L interactions in the generation of Th1 inflammatory responses. vCD30 may also provide alternative strategies to effectively block the activity of CD30 in vivo, which may be applied to modulate an over-reactive immune response in a number of human disease conditions (Gruss et al (1997) supra).

The invention claimed is:

1. A method of treatment of a Th1 mediated-inflammatory condition comprising administering a vCD30 polypeptide comprising an amino acid sequence having at least 90% sequence identity with SEQ ID NO: 1 and having vCD30 activity to an individual in need thereof, wherein vCD30 activity comprises one or more of the following properties: binding to CD30L, inducing signaling in cells expressing CD30L, inhibiting the binding of CD30 to CD30L, and inhibiting signaling in cells expressing CD30.

2. The method according to claim 1 wherein the vCD30 polypeptide comprises SEQ ID NO:1.

3. The method according to claim 1 wherein the vCD30 polypeptide comprises the amino acid sequence of SEQ ID NO:1 with substitutions at one or more of positions 38, 52, 70, 71, 86 and 93.

4. The method according to claim 1 wherein the vCD30 polypeptide comprises the amino acid sequence of SEQ ID NO:1 with one or more substitutions selected from the group consisting of: Lys38Thr, Ser52Pro, Met70Thr, Leu71Val, Thr86Ile and Glu93Asp.

5. The method according to claim 1 wherein the vCD30 polypeptide comprises the amino acid sequence of SEQ ID NO: 2 or SEQ ID NO: 3.

6. A method of making a pharmaceutical composition for use in the treatment of a Th1 mediated-inflammatory condition comprising admixing a vCD30 polypeptide comprising an amino acid sequence having at least 90% sequence identity with SEQ ID NO:1 and having vCD30 activity with a pharmaceutically acceptable excipient, vehicle or carrier, and optionally other ingredients, wherein the vCD30 activity comprises one or more of the following properties: binding to CD30L, inducing signaling in cells expressing CD30L, inhibiting the binding of CD30 to CD30L, and inhibiting signaling in cells expressing CD30.

7. The method according to claim 6 wherein the vCD30 polypeptide comprises SEQ ID NO:1.

8. The method according to claim 6 wherein the vCD30 polypeptide comprises the amino acid sequence of SEQ ID NO:1 with substitutions at one or more of positions 38, 52, 70, 71, 86 and 93.

9. The method according to claim 6 wherein the vCD30 polypeptide comprises the amino acid sequence of SEQ ID NO:1 with one or more substitutions selected from the group consisting of: Lys38Thr, Ser52Pro, Met70Thr, Leu71Val, Thr86Ile and Glu93Asp.

10. The method according to claim 6 wherein the vCD30 polypeptide comprises the amino acid sequence of SEQ ID NO:2 or SEQ ID NO:3.

* * * * *